US012269792B2

United States Patent
Galan et al.

(10) Patent No.: US 12,269,792 B2
(45) Date of Patent: *Apr. 8, 2025

(54) CRYSTALLINE 5-(DIMETHYLAMINO)-N-(4-(MORPHOLINOMETHYL) PHENYL)NAPHTHALENE-1-SULFONAMIDE DI-HYDROCHLORIDE DI-HYDRATE

(71) Applicant: GEN1E LIFESCIENCES INC., Palo Alto, CA (US)

(72) Inventors: Adam Galan, Alameda, CA (US); Ritu Lal, Palo Alto, CA (US); Wendy Luo, Palo Alto, CA (US)

(73) Assignee: GENIE LIFESCIENCES INC., Palo Alto, CA (US)

( * ) Notice: Subject to any disclaimer, the term of this patent is extended or adjusted under 35 U.S.C. 154(b) by 380 days.

This patent is subject to a terminal disclaimer.

(21) Appl. No.: 17/743,035

(22) Filed: May 12, 2022

(65) Prior Publication Data

US 2022/0267259 A1 Aug. 25, 2022

Related U.S. Application Data

(63) Continuation of application No. 17/506,822, filed on Oct. 21, 2021, now Pat. No. 11,390,581.

(60) Provisional application No. 63/106,991, filed on Oct. 29, 2020.

(51) Int. Cl.
C07C 311/29 (2006.01)

(52) U.S. Cl.
CPC ........ *C07C 311/29* (2013.01); *C07B 2200/13* (2013.01)

(58) Field of Classification Search
CPC .......................... C07C 311/29; C07B 2200/13
See application file for complete search history.

(56) References Cited

U.S. PATENT DOCUMENTS

| | | | |
|---|---|---|---|
| 3,594,386 A | 7/1971 | Regnier et al. | |
| 6,462,074 B1 | 10/2002 | Stolle et al. | |
| 8,173,684 B2 | 5/2012 | Kasahara et al. | |
| 11,078,171 B2 | 8/2021 | Shapiro et al. | |
| 11,286,260 B2 | 3/2022 | Galan et al. | |
| 11,357,781 B2 | 6/2022 | Shapiro et al. | |
| 11,390,581 B2* | 7/2022 | Galan | A61P 35/00 |
| 11,718,595 B2* | 8/2023 | Shapiro | C07D 295/03 |
| | | | 514/227.5 |
| 2005/0256133 A1 | 11/2005 | Lesur et al. | |
| 2007/0066616 A1 | 3/2007 | Shapiro et al. | |
| 2007/0208015 A1 | 9/2007 | Gill et al. | |
| 2010/0215618 A1 | 8/2010 | Carter et al. | |
| 2012/0172375 A1 | 7/2012 | Trapp et al. | |
| 2015/0357549 A1 | 12/2015 | Muller et al. | |
| 2019/0151324 A1 | 5/2019 | Shapiro et al. | |

FOREIGN PATENT DOCUMENTS

| | | |
|---|---|---|
| CN | 101675034 A | 3/2010 |
| CN | 105308004 A | 2/2016 |
| CN | 109640970 A | 4/2019 |
| DE | 19801646 A1 | 7/1999 |
| EP | 3474835 A1 | 5/2019 |
| GB | 2530598 | 3/2016 |
| JP | 2007-532615 | 11/2007 |
| JP | 2010-180234 | 8/2010 |
| JP | 2011-513288 | 4/2011 |
| JP | H11269146 | 10/2019 |
| JP | 7013453 B | 1/2022 |
| WO | 2004/065351 A1 | 8/2004 |
| WO | 2004/072077 A1 | 8/2004 |
| WO | 2005/100338 A1 | 10/2005 |
| WO | 2009/106844 A1 | 9/2009 |
| WO | 2010/082912 A1 | 7/2010 |
| WO | 2010/094977 A1 | 8/2010 |
| WO | 2015/121660 A1 | 8/2015 |
| WO | 2016/051155 A1 | 4/2016 |
| WO | 2016/073633 A1 | 5/2016 |
| WO | 2017/223284 A1 | 12/2017 |
| WO | 2018/119362 | 6/2018 |
| WO | 2020/118194 A1 | 6/2020 |
| WO | 2021/183970 A1 | 9/2021 |

OTHER PUBLICATIONS

International Preliminary Report on Patentability for Application No. PCT/US2019/064960, mailed on Jun. 17, 2021, 6 pages.
International Preliminary Report on Patentability for for Application No. PCT/US2017/038697, mailed on Dec. 25, 2018, 8 pages.
International Preliminary Report on Patentability for for Application No. PCT/US2021/032487, mailed on Dec. 1, 2022, 11 pages.
International Search Report and Written Opinion for Application No. PCT/US2019/064960, mailed on Feb. 25, 2020, 7 pages.
International Search Report and Written Opinion for Application No. PCT/US2017/038697, mailed on Oct. 31, 2017, 12 pages.
International Search Report and Written Opinion for Application No. PCT/US2021/032487, mailed on Sep. 22, 2021, 19 pages.
International Search Report and Written Opinion for Application No. PCT/US2021/055950, mailed on Dec. 14, 2021, 14 pages.
Extended European Search Report for Application No. EP 17816192, mailed on Mar. 30, 2020, 5 pages.
Non-Final Office Action for U.S. Appl. No. 16/312,499, mailed on Feb. 13, 2020, 8 pages.
Final Office Action for U.S. Appl. No. 16/312,499, mailed on May 21, 2020, 11 pages.
Non-Final Office Action for U.S. Appl. No. 17/231,598, mailed on Jun. 29, 2021, 9 pages.

(Continued)

*Primary Examiner* — Amanda L. Aguirre
*Assistant Examiner* — William Y Lee

(57) ABSTRACT

Crystalline 5-(dimethylamino)-N-(4-(morpholinomethyl) phenyl)naphthalene-1-sulfonamide dihydrochloride dihydrate, methods of preparing the crystalline salt, pharmaceutical compositions containing the crystalline salt, and methods of treatment using the crystalline salt are disclosed.

20 Claims, 10 Drawing Sheets

(56) References Cited

OTHER PUBLICATIONS

Non-Final Office Action for U.S. Appl. No. 16/872,114, mailed on Dec. 7, 2020, 7 pages.
Biava et al., "Synthesis and Antimycobacterial Activity of New Amidoderivatives of Ortho-, Meta- and Para-Toluidine", Medicinal Chemistry Research, Jan. 1998, vol. 8, No. 9, pp. 523-541.
Biava et al., "Antimycobacterial activity of new ortho-, meta- and para-toluidine derivatives", II Farmaco, 1999, vol. 54, pp. 721-727.
Chemical Abstract STN Registry Database record for RN 2337349-33-2, entered into STN Jun. 17, 2019.
Chemical Abstract STN Registry Database Record for RN 1293859-67-2, STN Entered May 12, 2011.
Cheng et al., "Identification and Optimization of New Dual Inhibitors of B-Raf and Epidermal Growth Factor Receptor Kinases for Overcoming Resistance against Vemurafenib", Journal of Medicinal Chemistry, American Chemical Society, 2014, vol. 57, pp. 2692-2703.
CAS 2337349-33-2 retrieved on Jun. 17, 2019.
CAS 255713-96-3 retrieved on Feb. 10, 2000.
CAS 697229-25-7 retrieved on Jun. 22, 2004.
Chemical Abstract STN Registry Database, Record for RN 1587574-74-0, "N-[4-[(4-Chlorobenzoyl)amino]phenyl]-2-oxo-1-piperazineacetamide hydrochloride", entered on Apr. 21, 2014.
Caira, Mino R. "Crystalline Polymorphism of Organic Compounds", Topics in Current Chemistry, Jan. 1998, vol. 198, pp. 163-208.
Haller et al., "An updated patent review of p38 MAP kinase inhibitors (2014-2019)", Expert Opinion on Therapeutics Patents, 2020, vol. 30, No. 6, p. 453-466.
Kheiri et al., "Role pf p38/MAPKs in Alzheimer's disease: implications for amyloid beta toxicity targeted therapy", Reviews in Neuroscience, 2018, vol. 30, No. 1, pp. 9-30.
Koroleva et al., "Synthesis of new amides of the N-methylpiperazine series", Russian Journal of Organic Chemistry, Nauka/Interperiodica, Nov. 2011, vol. 47, No. 10, pp. 1556-1563.
Lee et al., "Docketing-based 3D-QSAR study for 11β-HSD1 inhibitors", Bioorganic & Medicinal Chemistry Letters, 2008, vol. 18, pp. 2479-2490.
Mavropoulos et al., "p38 mitogen-activated protein kinase (p38 MAPK)-mediated autoimmunity: Lessons to learn from ANCA vasculitis and pemphigus vulgaris", Autoimmunity Reviews, Mar. 2013, vol. 12, Issue 5, pp. 580-590.
Nagao et al., "Synthesis and structure-activity relationships of novel, potent, orally active hypoxia-inducible factor-1 inhibi", Bioorganic & Medicinal Chemistry, Jul. 2014, vol. 22, No. 19, pp. 5513-5529.
Pubchem CID 899207 created Jul. 9, 2005, accessed on Feb. 5, 2020, 9 pages.
Pubchem, Substance Database SID 105140242, available on Feb. 22, 2011, retrieved on Aug. 8, 2017, retrieved from https://pubchem.ncbi.nlm.nih.gov/substance/105140242.
Sasindran et al., "*Mycobacterium* Tuberculosis Infection and Inflammation: what is Beneficial for the Host and for the Bacterium?", Frontiers in Microbiology, Jan. 2011, vol. 2, Article 2, 33 pages.
Segales et al., "Regulation of Muscle Stem Cell Functions: A Focus on the p38 MAPK Signaling Pathway", Frontiers in Cell and Developmental Biology, Aug. 2016, vol. 4, Article 91, 15 pages.
Shah et al., "Novel Noncatalytic Substrate-Selective p38[alpha]-Specific MAPK Inhibitors with Endothelial-Stabilizing and Anti-Inflammatory Activity", The Journal of Immunology, Mar. 2017, vol. 198, No. 8, pp. 3296-3306.
Wang et al., "Chapter 2—A Structural Atlas of Kinases Inhibited by Clinically Approved Drugs", Methods of Enzymology, 2014, vol. 548, pp. 23-67.
Yong et al., "The p38 MAPK inhibitors for the treatment of inflammatory diseases and cancer", Expert Opinion on Investigational Drugs, Oct. 2009, ISSN 1354-3784, vol. 18, No. 12, pp. 1893-1905.
International Preliminary Report on Patentability for for Application No. PCT/US2021/055950, mailed on May 11, 2023, 7 pages.
Chemical Abstract STN Registry Database Record for RN 851167-79-8, Entered STN May 26, 2005.
Chemical Abstract STN Registry Database Record for RN 2331174-12-8, Entered STN Jun. 12, 2019.
Chemical Abstract STN Registry Database Record for RN 2338713-47-7, Entered STN Jun. 18, 2019.
Chemical Abstract STN Registry Database Record for RN 2347052-15-5, Entered STN Jun. 27, 2019.
International Search Report and Written Opinion for Application No. PCT/US2022/021181, mailed on Jun. 28, 2022, 15 pages.

* cited by examiner

CRYSTALLINE 5-(DIMETHYLAMINO)-N-(4-(MORPHOLINOMETHYL) PHENYL)NAPHTHALENE-1-SULFONAMIDE DI-HYDROCHLORIDE DI-HYDRATE

This application is a continuation of U.S. application Ser. No. 17/506,822, filed on Oct. 21, 2021, now allowed, which claims the benefit under 35 U.S.C. § 119(e) of U.S. Provisional Application No. 63/106,991 filed on Oct. 29, 2020, which is incorporated by reference in its entirety.

FIELD

The invention relates to crystalline 5-(dimethylamino)-N-(4-(morpholinomethyl)phenyl)naphthalene-1-sulfonamide dihydrochloride dihydrate, methods of preparing the crystalline salt, pharmaceutical compositions containing the crystalline salt, and methods of treatment using the crystalline salt.

BACKGROUND

Mitogen-activated protein kinases (MAPKs) are serine/threonine protein kinases that process and regulate cellular properties in response to a wide range of extracellular stimuli. These enzymes phosphorylate the OH group of serine or threonine in proteins and play important roles in the regulation of cell proliferation, differentiation, survival, and apoptosis. In mammalian cells, several distinct MAPKs have been identified, including p38 MAPK.

p38 MAPK is a class of MAPKs responsive to stress stimuli such as inflammatory cytokines and reactive oxygen species (ROS) and is involved in a wide range of signaling pathways that stimulate different biological functions. For example, p38 MAPK plays an essential role in the regulation of pro-inflammatory signaling networks and in the biosynthesis of cytokines, including tumor necrosis factor-α (TNF-α) and interleukin-1β (IL-1β) in immune cells.

Studies have shown that p38 MAPK contributes to the pathogenesis of chronic inflammation, which has led to the identification and development of p38 MAPK inhibitors for treating inflammatory diseases such as rheumatoid arthritis and asthma.

p38 MAPK comprises four isoforms (α, β, γ and δ). p38α MAPK was the first isoform of p38 MAPK to be identified and was first recognized as a stress-induced kinase that can be activated by lipopolysaccharide (LPS) and inflammatory cytokines. Inhibition of p38 MAPK has been shown to effectively alleviate inflammatory diseases such as rheumatoid arthritis, cardiovascular disease, and inflammatory pain.

Many p38 MAPK catalytic inhibitors are poorly effective and cause toxicity, possibly due to activity against non-inflammatory p38 and loss of p38α-dependent counterregulatory responses. p38α MAPK inhibitors that can selectively block certain p38α MAPK functions and preserve critical counterregulatory and homeostatic functions with application for the treatment of inflammatory and oncologic diseases are desired.

SUMMARY

According to the present invention a compound is crystalline 5-(dimethylamino)-N-(4-(morpholinomethyl)phenyl) naphthalene-1-sulfonamide dihydrochloride dihydrate:

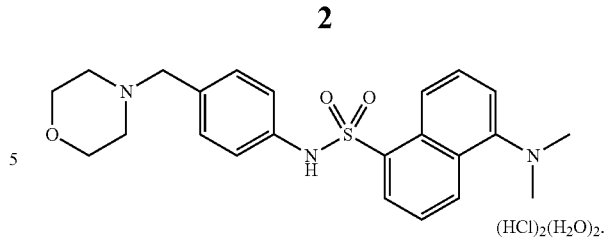

$(HCl)_2(H_2O)_2$.

According to the present invention a pharmaceutical composition comprises compound (1).

According to the present invention methods of treating a disease in a patient comprise administering to a patient in need of such treatment a therapeutically effective of amount of compound (1), wherein the disease is cancer.

According to the present invention methods of treating a disease in a patient comprise administering to a patient in need of such treatment a therapeutically effective of amount of compound (1), wherein the disease is an inflammatory disease.

According to the present invention methods of treating a disease in a patient comprise administering to a patient in need of such treatment a therapeutically effective of amount of compound (1), wherein the disease is an autoimmune disease.

According to the present invention methods of treating a disease in a patient comprise administering to a patient in need of such treatment a therapeutically effective of amount of compound (1), wherein the disease is an age-related disease.

According to the present invention methods of treating a disease in a patient comprise administering to a patient in need of such treatment a therapeutically effective of amount of compound (1), wherein the disease is selected from acute lung injury, acute respiratory distress syndrome (ARDS), and chronic obstructive pulmonary disease (COPD).

According to the present invention methods of inhibiting the p38α MAPK receptor comprise contacting the p38α MAPK receptor with compound (1).

According to the present invention methods of inhibiting the p38α MAPK receptor in a patient comprise administering to a patient a pharmacologically effective amount of compound (1).

BRIEF DESCRIPTION OF THE DRAWINGS

The drawings described herein are for illustration purposes only. The drawings are not intended to limit the scope of the present disclosure.

DETAILED DESCRIPTION

Figure 1:
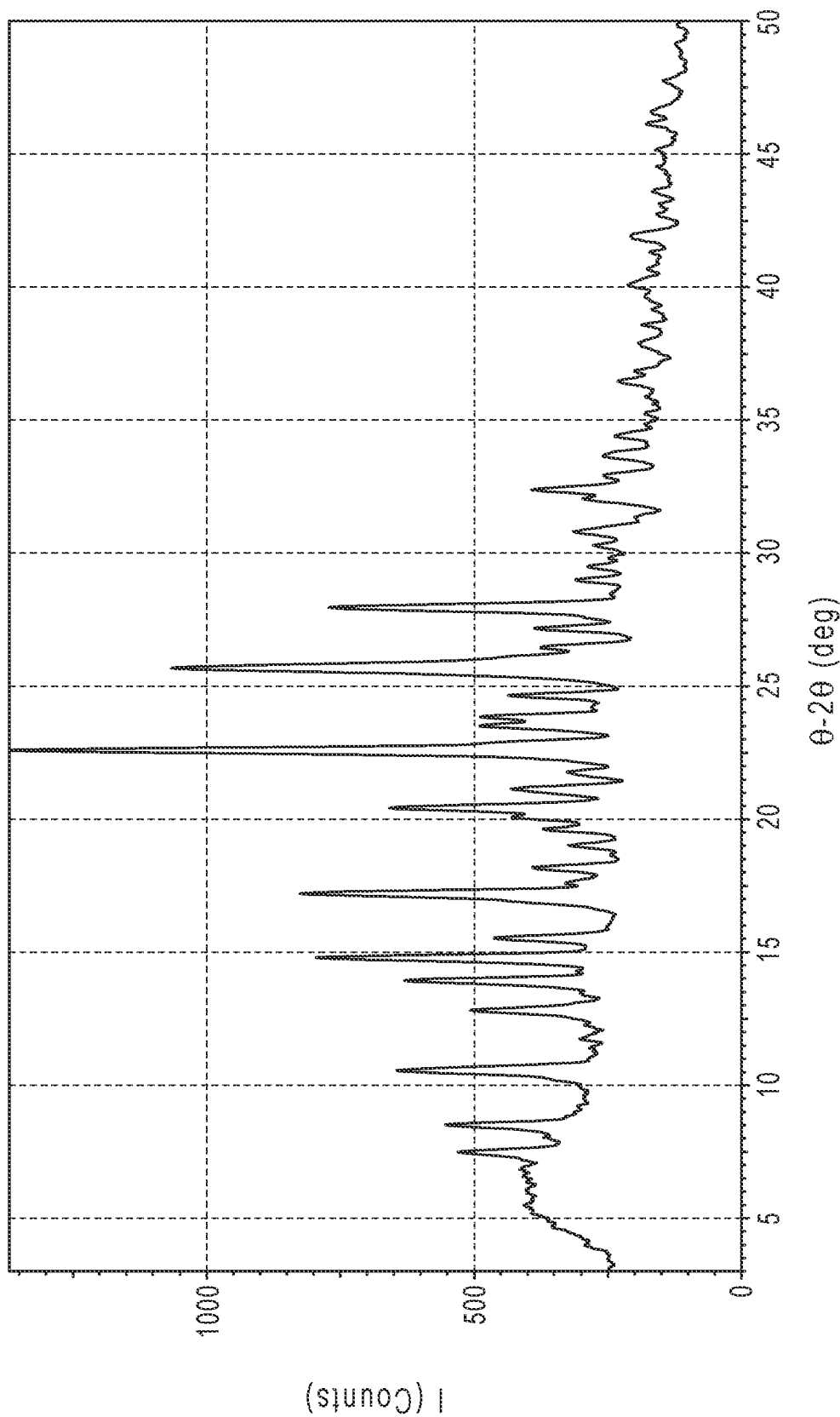
FIG. 1 shows an X-ray powder diffraction (XRPD) pattern of crystalline 5-(dimethylamino)-N-(4-(morpholinomethyl) phenyl)naphthalene-1-sulfonamide dihydrochloride dihydrate (compound (1)).

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. [30] "Compounds" and moieties disclosed herein include any specific compounds within the disclosed formula. Compounds may be identified either by chemical structure and/or by chemical name. Compounds are named using the ChemDraw Professional 17.1.0.105 (19) (PerkinElmer Informatics, Inc.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

Crystalline 5-(dimethylamino)-N-(4-(morpholinomethyl) phenyl)naphthalene-1-sulfonamide dihydrochloride dihydrate is also referred to as the "crystalline dihydrochloride dihydrate" or the "crystalline salt" for convenience.

"Immediate release" refers to a pharmaceutical composition that releases substantially all of an pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions include controlled release formulations, delayed release formulations, extended release formulations, sustained release formulations, timed release formulations, pulsatile release formulations, and pH-dependent release formulations. These formulations are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The USP defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

"Sustained release" pharmaceutical compositions and coating provide for a dissolution rate over an extended period of time following oral administration. Granulations comprising granules having a sustained release coating can be referred to as sustained release granulations. A pharmaceutical composition comprising a sustained release granulation can be referred to as a sustained release pharmaceutical composition.

"pH-release" pharmaceutical compositions and coatings provide for an increased dissolution rate at an intended pH.

"Pulsatile release" pharmaceutical compositions and coatings exhibit an increased dissolution rate at intervals, where the release intervals can be determined by time, exposure to internal stimuli, or exposure to external stimuli. Examples of pulsatile-release systems include capsular systems, osmotic systems, systems having erodible membranes, and systems having a rupturable coating. Examples of stimuli include temperature, chemicals, electrical stimuli, and magnetic stimuli.

"Timed-release" pharmaceutical compositions and coatings have a dissolution rate that is a function of time. A time-release pharmaceutical composition or coating includes, for example, delayed release, sustained release, and extended release pharmaceutical compositions and coatings.

"Delayed release" pharmaceutical compositions and coatings provide for an increased dissolution rate at an intended time after administration.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule. For example, compound (2) can modulate the p38α MAPK protein such as inhibit p38α MAPK protein. Compound (2) can selectively modulate such as selectively inhibit p38α MAPK protein as compared to other MAPK or p38 MAPK proteins. Compound (2) can selectively modulate such as selectively inhibit p38α MAPK protein as compared to other MAPK or p38 MAPK proteins.

"Moiety" refers to a specific segment or functional group of a molecule. Chemical moieties are often recognized chemical entities embedded within or appended to a molecule.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to compound (1) and at least one pharmaceutically acceptable vehicle, with which compound (1) is administered to a patient. Pharmaceutically acceptable vehicles are known in the art.

"Disease" refers to a disease, disorder, condition, or symptom of any of the foregoing.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Curing" a disease refers to eliminating a disease or disorder or eliminating a symptom of a disease or disorder.

"Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, reducing the severity of one or more clinical symptom of the disease or disorder, delaying the onset of one or more clinical symptoms of the disease or disorder, mitigating one or more clinical symptoms of the disease or disorder and/or stabilizing the disease or disorder or one or more clinical symptoms of the disease or disorder. "Treating" or "treatment" of a disease or disorder includes producing a clinically beneficial effect without curing the underlying disease or disorder.

"Therapeutically effective amount" refers to the amount of a compound such as pharmaceutically active ingredient that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made to crystalline 5-(dimethylamino)-N-(4-(morpholinomethyl)phenyl)naphthalene-1-sulfonamide dihydrochloride dihydrate, methods of making the crystalline salt, pharmaceutical compositions comprising the crystalline salt, and uses of the crystalline salt. The disclosed crystalline salt, pharmaceutical compositions, methods, and uses are not intended to be limiting of the claims. To the contrary, the claims are intended to cover all alternatives, modifications, and equivalents.

Compound (1), crystalline 5-(dimethylamino)-N-(4-(morpholinomethyl)phenyl)naphthalene-1-sulfonamide dihydrochloride dihydrate, is a stable salt of 5-(dimethylamino)-N-(4-(morpholinomethyl)phenyl)naphthalene-1-sulfonamide, compound (2). Compound (1) has the structure:

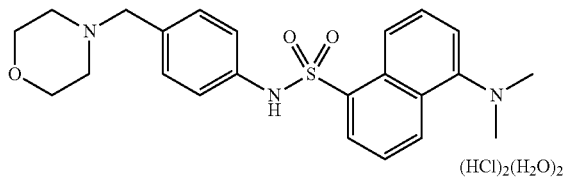

(1)

$(HCl)_2(H_2O)_2$ 5-(Dimethylamino)-N-(4-(morpholinomethyl)phenyl)naphthalene-1-sulfonamide is a substrate selective p38α MAPK inhibitor. 5-(Dimethylamino)-N-(4-(morpholinomethyl)phenyl)naphthalene-1-sulfonamide (free base, Compound 2) has the structure of Formula (2):

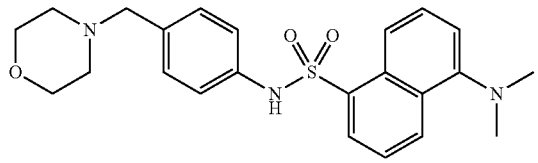

(2)

Methods of synthesizing compound (2) and properties of compound (2) are disclosed in PCT International Publication No. WO 2020/118194.

Compound (1), crystalline 5-(dimethylamino)-N-(4-(morpholinomethyl)phenyl)naphthalene-1-sulfonamide dihydrochloride dihydrate, is a stable salt of free base compound (2).

Crystalline 5-(dimethylamino)-N-(4-(morpholinomethyl) phenyl)naphthalene-1-sulfonamide dihydrochloride dihydrate salt can be prepared as described in Example 1.

Compound (1) can be characterized by an XRPD pattern comprising characteristic diffraction peaks at least at 10.5°±0.2°, 13.9°±0.2°, 14.8°±0.2°, 17.2°±0.2°, 20.4°±0.2°, 22.6°±0.2°, 25.7°±0.2°, and 27.9°±0.2° expressed as 2θ angles and determined using Cu-Kα radiation.

Compound (1) can be characterized by an XRPD pattern comprising characteristic diffraction peaks at least at 10.5°±0.1°, 13.9°±0.1°, 14.8°±0.1°, 17.2°±0.1°, 20.4°±0.1°, 22.6°±0.1°, 25.7°±0.1°, and 27.9°±0.2° expressed as 2θ angles and determined using Cu-Kα radiation.

Compound (1) can be characterized by an XRPD pattern comprising characteristic diffraction peaks at least at 7.5°±0.2°, 8.5°±0.2°, 10.5°±0.2°, 12.8°±0.2°, 13.9°±0.2°, 14.8°±0.2°, 15.5°±0.2°, 17.2°±0.2°, 18.2°±0.2°, 20.1°±0.2°, 20.4°±0.2°, 21.1°±0.2°, 22.6°±0.2°, 22.9°±0.2°, 23.5°±0.2°, 23.8°±0.2°, 24.6°±0.2°, 25.7°±0.2°, 26.1°±0.2°, 26.4°±0.2°, 27.1°±0.2°, 27.5°±0.2°, 27.9°±0.2°, and 32.4°±0.2° expressed as 2θ angles and determined using Cu-Kα radiation.

Compound (1) can be characterized by an XRPD pattern comprising characteristic diffraction peaks at least at 7.5°±0.1°, 8.5°±0.1°, 10.5°±0.1°, 12.8°±0.1°, 13.9°±0.1°, 14.8°±0.1°, 15.5°±0.1°, 17.2°±0.1°, 18.2°±0.1°, 20.1°±0.1°, 20.4°±0.1°, 21.1°±0.1°, 22.6°±0.1°, 22.9°±0.1°, 23.5°±0.1°, 23.8°±0.1°, 24.6°±0.1°, 25.7°±0.1°, 26.1°±0.1°, 26.4°±0.1°, 27.1°±0.1°, 27.5°±0.1°, 27.9°±0.1°, and 32.4°±0.1° expressed as 2θ angles and determined using Cu-Kα radiation.

Compound (1) can be characterized by an XRPD pattern as substantially shown in FIG. 1.

Compound (1) can have a melting onset temperature, for example, from 161° C. to 167° C., such as from 162° C. to 166° C., or from 163° C. to 165° C., where the melting onset temperature is determined by differential scanning calorimetry.

Compound (1) can have a melting onset temperature, for example, of 164.3° C.±0.5° C., such as 164.3° C.±0.25° C., or 164.3° C.±0.1° C., where the melting onset temperature is determined by differential scanning calorimetry.

Compound (1) can have a melting enthalpy, for example, from 89 J/g to 99 J/g, from 91 J/g to 97 J/g, or from 93 J/g to 95 J/g, where the melting enthalpy is determined by differential scanning calorimetry.

Compound (1) can have a melting enthalpy, for example, of 94.25 J/g±0.5 J/g, such as 94.2 J/g±0.25 J/g, or 94.2 J/g±0.1 J/g, where the melting enthalpy is determined by differential scanning calorimetry.

Compound (1) can have a melting peak, for example, from 178.5 J/g to 184.5 J/g, from 179.5 J/g to 183.5 J/g, or from 179.5 J/g to 182.5 J/g, where the melting peak is determined by differential scanning calorimetry.

Figure 2:
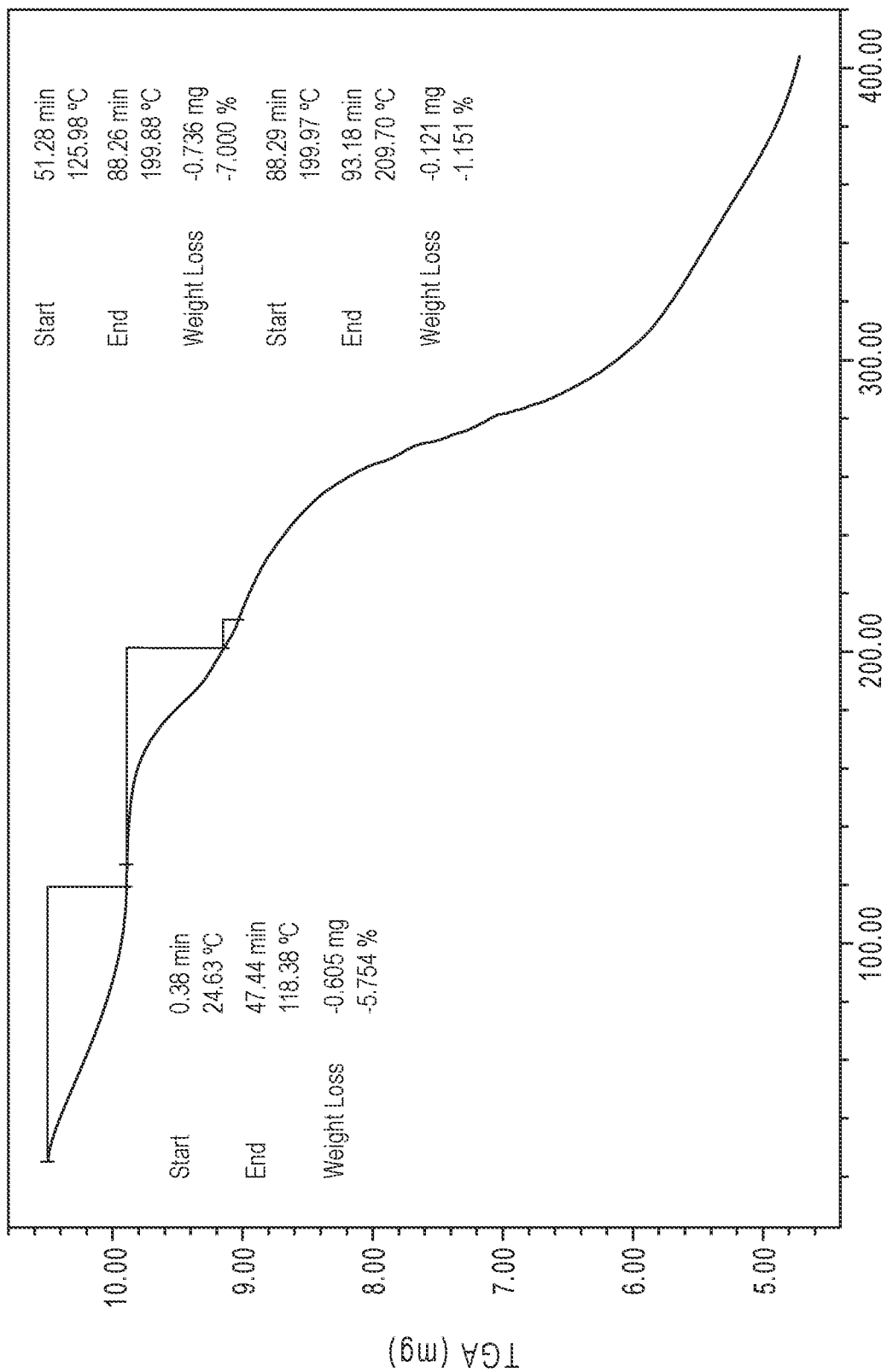
FIG. 2 shows a differential scanning calorimetry (DSC) scan of compound (1).

Compound (1) can have a melting peak, for example, at 181.6° C.±2.0° C., such as 181.6° C. ±1.0° C., or 181.6° C.±05° C., where the melting peak is determined by differential scanning calorimetry. [71] Compound (1) can exhibit a differential scanning calorimetry curve as substantially shown in FIG. 2.

Compound (1) can have a weight loss, for example, from 13% to 15% at a temperature from 25° C. to 210° C., such as from 13.3% to 14.7% at a temperature from 25° C. to 210° C., or from 13.6% to 14.4% at a temperature from 25° C. to 210° C., where the weight loss is determined by thermogravimetric analysis at a scan rate of 2° C./min.

Compound (1) can have a weight loss, for example, of 13.9%±1.0%, such as 13.9%±0.5%, or 13.9%±0.2% at a temperature from 25° C. to 210° C., where the weight loss is determined by thermogravimetric analysis at a scan rate of 2° C./min.

Figure 3:
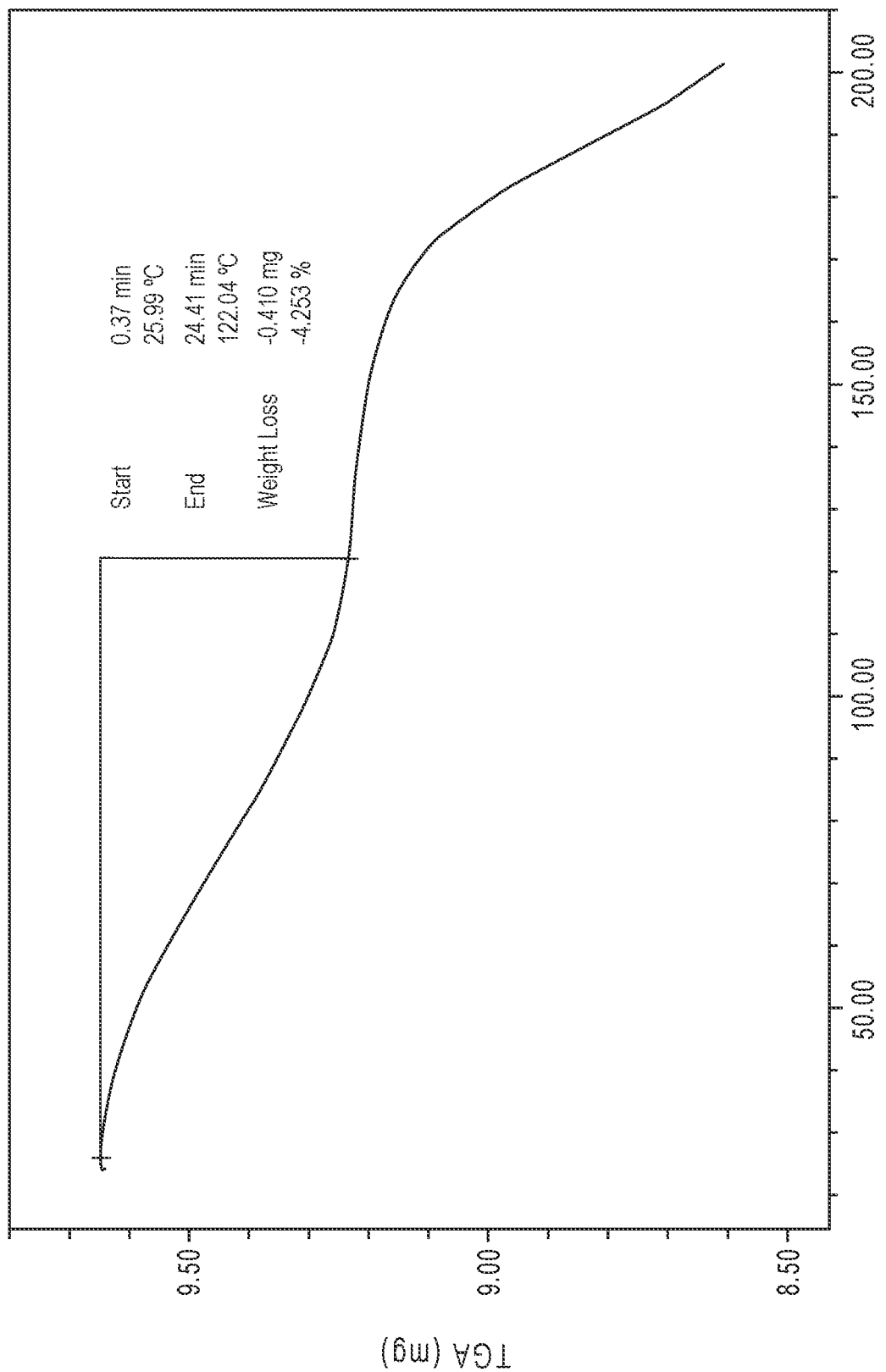
FIG. 3 shows a thermogravimetric analysis (TGA) scan of compound (1) at a scan rate of 2° C./min.

Compound (1) provided by the present disclosure can exhibit a differential thermal calorimetry curve as substantially shown in FIG. 3.

Compound (1) can have a weight loss, for example, from 2% to 6% at a temperature from 25° C. to 122° C., such as from 3% to 5% at a temperature from 25° C. to 122° C., or from 3.75% to 4.75% at a temperature from 25° C. to 122°

C., where the weight loss is determined by thermogravimetric analysis at a scan rate of 4.25° C./min.

Compound (1) can have a weight loss, for example, of 4.25%±1.0%, such as 4.25%±0.5%, or 4.25%±0.2% at a temperature from 25° C. to 122° C., where the weight loss is determined by thermogravimetric analysis at a scan rate of 4.25° C./min.

Figure 4:
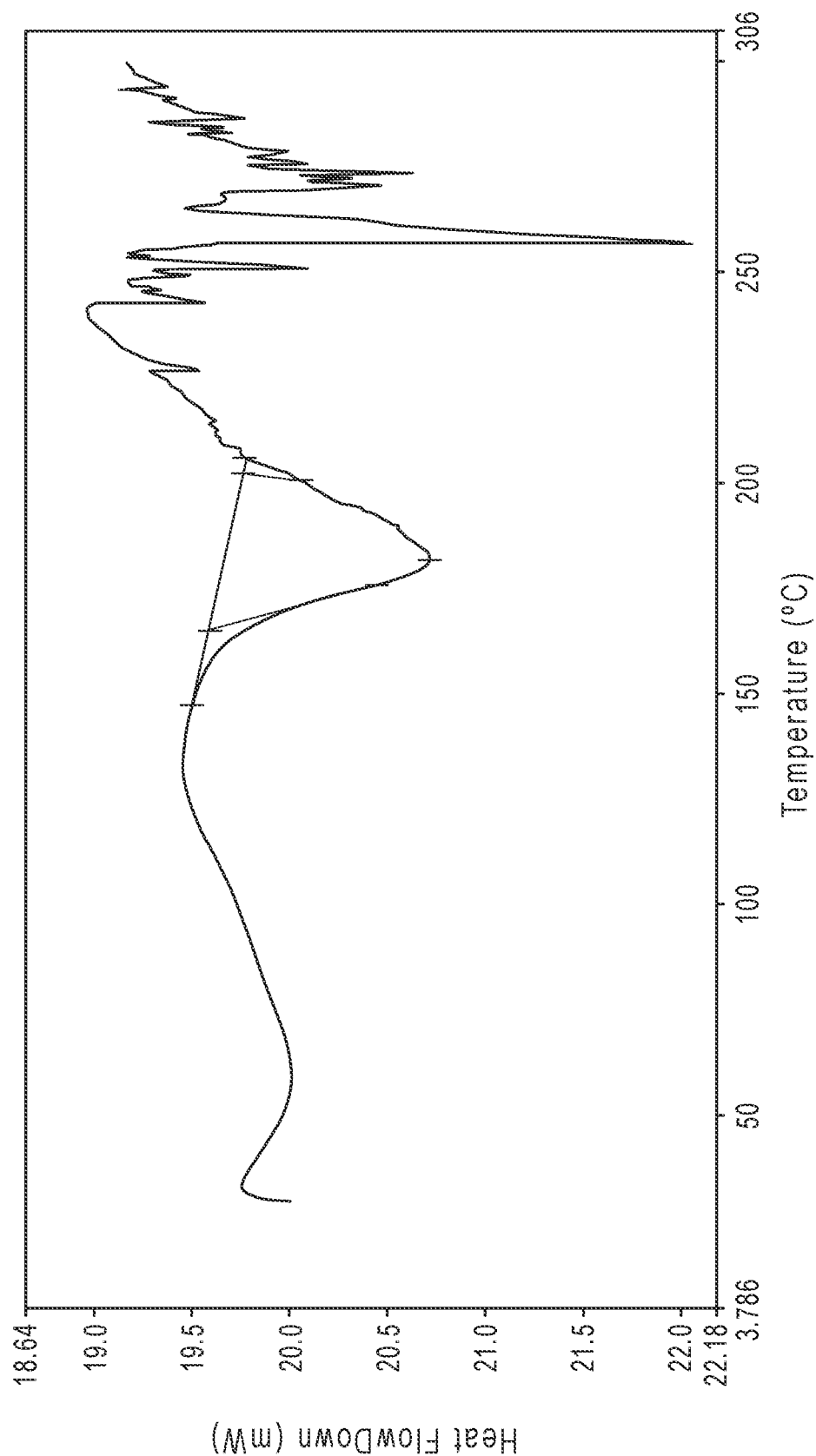
FIG. 4 shows a thermogravimetric analysis (TGA) scan of compound (1) at a scan rate of 4° C./min.

Compound (1) provided by the present disclosure can exhibit a differential thermal calorimetry curve as substantially shown in FIG. 4.

Compound (1) can have a water content, for example, from 5.8 mol % to 6.6 mol %, such as from 5.9 mol % to 6.5 mol %, form 6.0 mol % to 6.4 mol %, from 6.1 mol % to 6.3 wt %, or 6.2 mol %, where mol % is based on the total moles of compound (1).

5-(Dimethylamino)-N-(4-(morpholinomethyl)phenyl) naphthalene-1-sulfonamide, free base, can be prepared as described in PCT International Publication No. WO 2020/118194.

Figure 5:
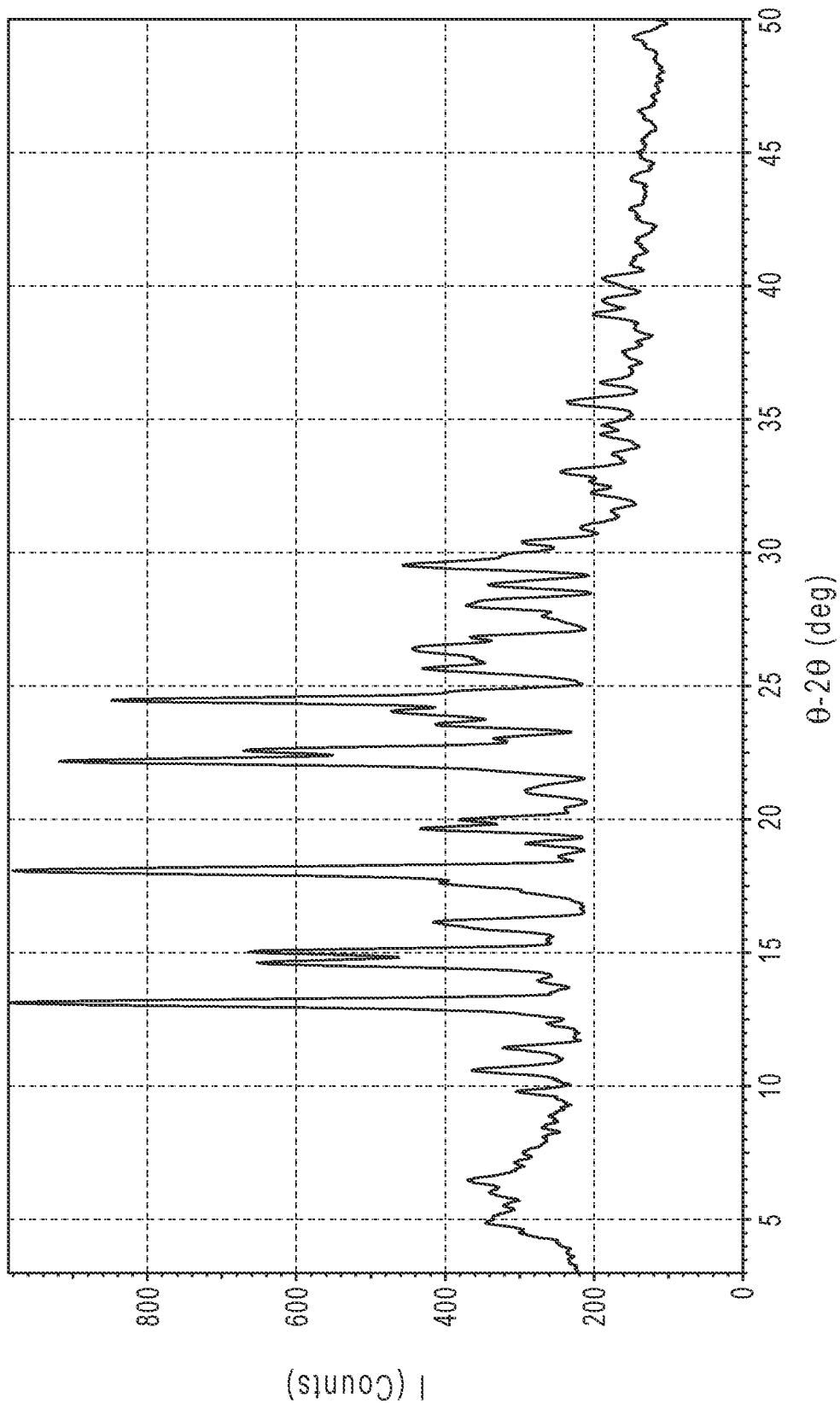
FIG. 5 shows an X-ray powder diffraction (XRPD) pattern of crystalline anhydrous 5-(dimethylamino)-N-(4-(morpholinomethyl)phenyl)naphthalene-1-sulfonamide dihydrochloride.

An XRPD pattern of crystalline anhydrous compound (2) is shown in FIG. 5.

Compound (2) can be characterized by an XRPD pattern comprising characteristic diffraction peaks at least at 13.1°±0.2°, 14.6°±0.2°, 15.0°±0.2°, 18.1±0.2°, 22.2±0.2°, 22.6±0.2°, and 24.4±0.2° expressed as 2θ angles and determined using Cu-Kα radiation.

Compound (2) can be characterized by an XRPD pattern comprising characteristic diffraction peaks at least at 13.1°±0.1°, 14.6°±0.1°, 15.0°±0.1°, 18.1±0.1°, 22.2±0.1°, 22.6±0.1°, and 24.4±0.1° expressed as 2θ angles and determined using Cu-Kα radiation.

Compound (2) can have a primary melting onset temperature, for example, from 158° C. to 164° C., such as from 159° C. to 163° C., or from 160° C. to 162° C., where the melting onset temperature is determined by differential scanning calorimetry.

Compound (2) can have a primary melting onset temperature, for example, of 160.9° C.±0.5° C., such as 160.9° C.±0.25° C., or 160.9° C.±0.1° C., where the melting onset temperature is determined by differential scanning calorimetry.

Compound (2) can have a primary melting enthalpy, for example, from 60 J/g to 65 J/g, from 61 J/g to 65 J/g, or from 62 J/g to 4 J/g, where the melting enthalpy is determined by differential scanning calorimetry.

Compound (2) can have a primary melting enthalpy, for example, of 62.8 J/g±0.5 J/g, such as 62.8 J/g±0.25 J/g, or 62.8 J/g±0.1 J/g, where the melting enthalpy is determined by differential scanning calorimetry.

Compound (2) can have a primary melting peak, for example, from 175 J/g to 182 J/g, from 176 J/g to 181 J/g, or from 177 J/g to 180 J/g, where the melting peak is determined by differential scanning calorimetry.

Compound (2) can have a primary melting peak, for example, at 177.8° C.±2.0° C., such as 177.8° C.±1.0° C., or 177.8° C.±0.5° C., where the melting peak is determined by differential scanning calorimetry.

Compound (2) can have a secondary melting onset temperature of 204.7° C., a secondary melting enthalpy of 20.7 J/g, and a secondary melting peak at 211.2° C.

Figure 6:
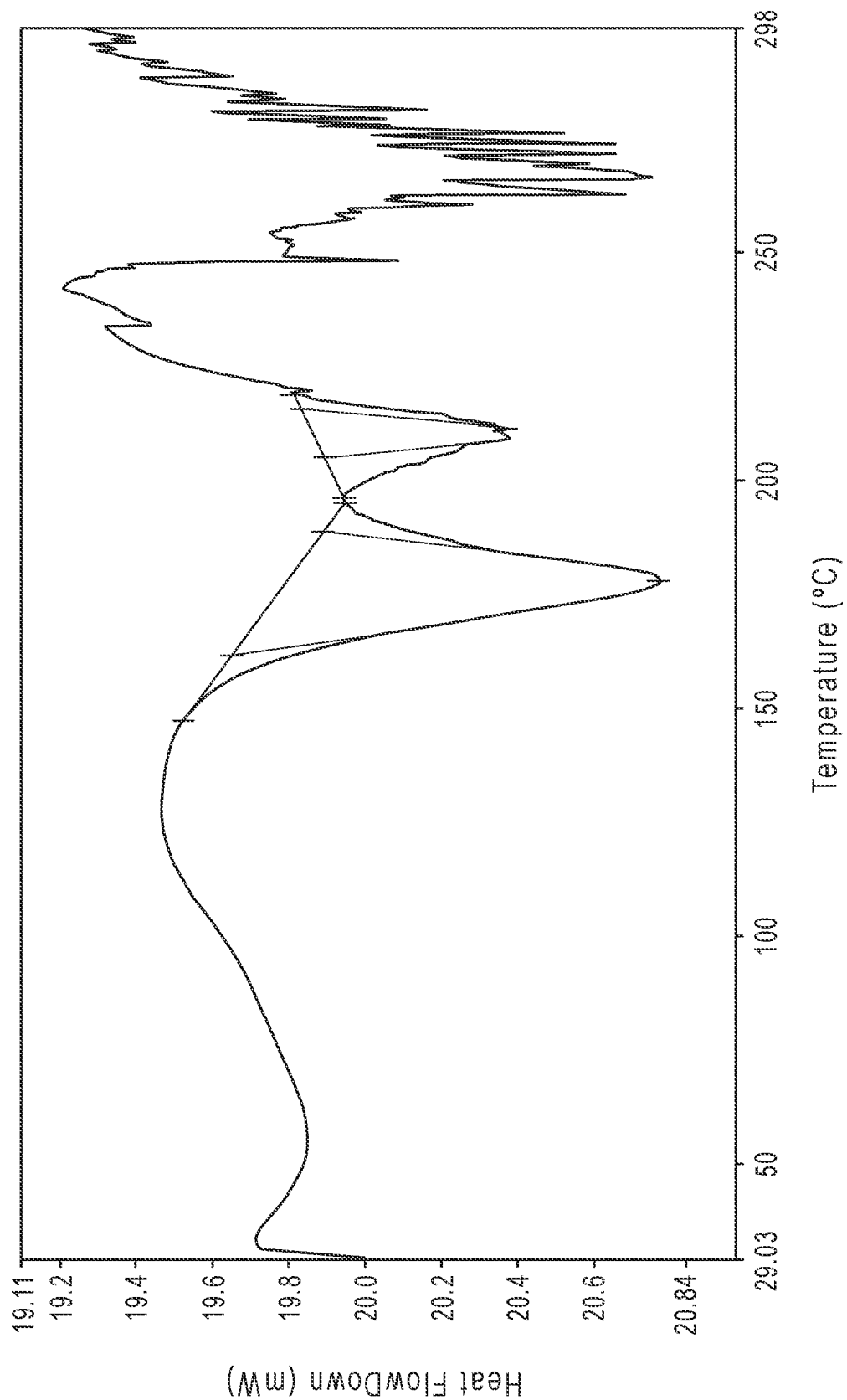
FIG. 6 shows an X-ray powder diffraction (XRPD) pattern of crystalline 5-(dimethylamino)-N-(4-(morpholinomethyl) phenyl)naphthalene-1-sulfonamide dihydrochloride monohydrate prepared by exposing crystalline anhydrous 5-(dimethylamino)-N-(4-(morpholinomethyl)phenyl) naphthalene-1-sulfonamide dihydrochloride to atmospheric moisture.

Compound (2) can exhibit a differential scanning calorimetry curve as substantially shown in FIG. 6.

Crystalline 5-(dimethylamino)-N-(4-(morpholinomethyl)phenyl)naphthalene-1-sulfonamide dihydrochloride monohydrate (compound (3)) can result by exposing crystalline 5-(dimethylamino)-N-(4-(morpholinomethyl)phenyl)naphthalene-1-sulfonamide dihydrochloride to moisture. The dihydrochloride monohydrate can have a water content of 3.9 mol %.

Figure 7:
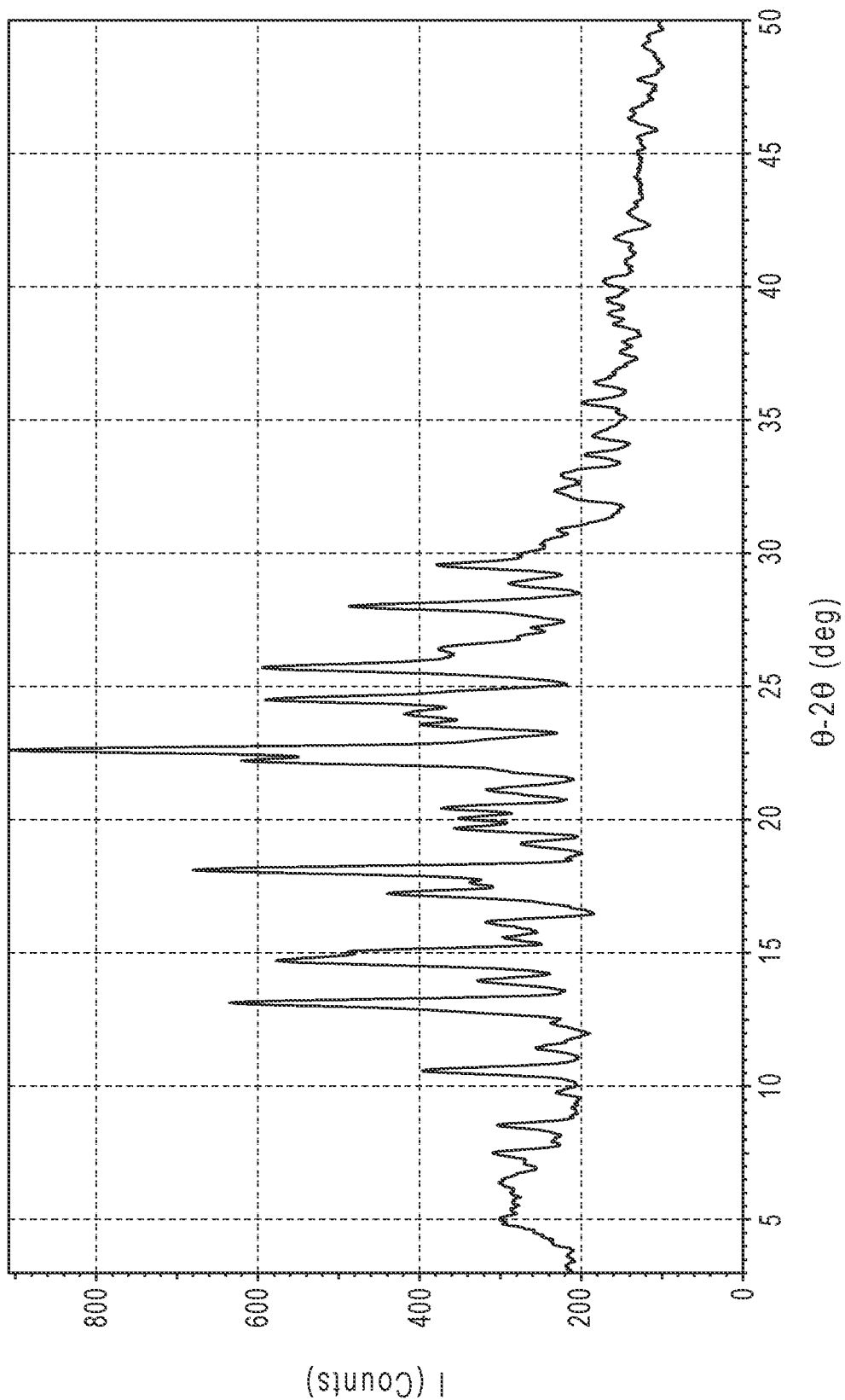
FIG. 7 shows a differential scanning calorimetry (DSC) scan of crystalline anhydrous 5-(dimethylamino)-N-(4-(morpholinomethyl)phenyl)naphthalene-1-sulfonamide dihydrochloride.

An XRPD pattern of 5-(dimethylamino)-N-(4-(morpholinomethyl)phenyl)naphthalene-1-sulfonamide dihydrochloride monohydrate is shown in FIG. 7.

The dihydrochloride monohydrate can be characterized by an XRPD pattern comprising characteristic diffraction peaks at least at 13.1°±0.2°, 14.7°±0.2°, 18.1°±0.2°, 22.2±0.2°, 22.6±0.2°, 24.5±0.2°, and 25.7±0.2° expressed as 2θ angles and determined using Cu-Kα radiation.

The dihydrochloride monohydrate can be characterized by an XRPD pattern comprising characteristic diffraction peaks at least at 13.1°±0.1°, 14.7°±0.1°, 18.1°±0.1°, 22.2±0.1°, 22.6±0.1°, 24.5±0.1°, and 25.7±0.1° expressed as 2θ angles and determined using Cu-Kα radiation.

The dihydrochloride monohydrate can have a melting onset temperature, for example, from 159° C. to 166° C., such as from 160° C. to 165° C., or from 161° C. to 164° C., where the melting onset temperature is determined by differential scanning calorimetry.

The dihydrochloride monohydrate can have a melting onset temperature, for example, of 162.9° C.±0.5° C., such as 162.9° C.±0.25° C., or 162.9° C.±0.1° C., where the melting onset temperature is determined by differential scanning calorimetry.

The dihydrochloride monohydrate can have a melting enthalpy, for example, from 92 J/g to 98 J/g, from 93 J/g to 97 J/g, or from 94 J/g to 96 J/g, over a temperature range from 163° C. to 194° C., where the melting enthalpy is determined by differential scanning calorimetry.

The dihydrochloride monohydrate can have a melting enthalpy, for example, of 94.9 J/g±0.5 J/g, such as 94.9 J/g±0.25 J/g, or 94.9 J/g±0.1 J/g, over a temperature range from 163° C. to 194° C., where the melting enthalpy is determined by differential scanning calorimetry.

The dihydrochloride monohydrate can have a melting peak, for example, from 175 J/g to 182 J/g, from 176 J/g to 181 J/g, or from 177 J/g to 180 J/g, where the melting peak is determined by differential scanning calorimetry.

The h dihydrochloride monohydrate can have a melting peak, for example, at 178.0° C.±2.0° C., such as 178.0° C.±1.0° C., or 178.0° C.±0.5° C., where the melting peak is determined by differential scanning calorimetry.

Figure 8:
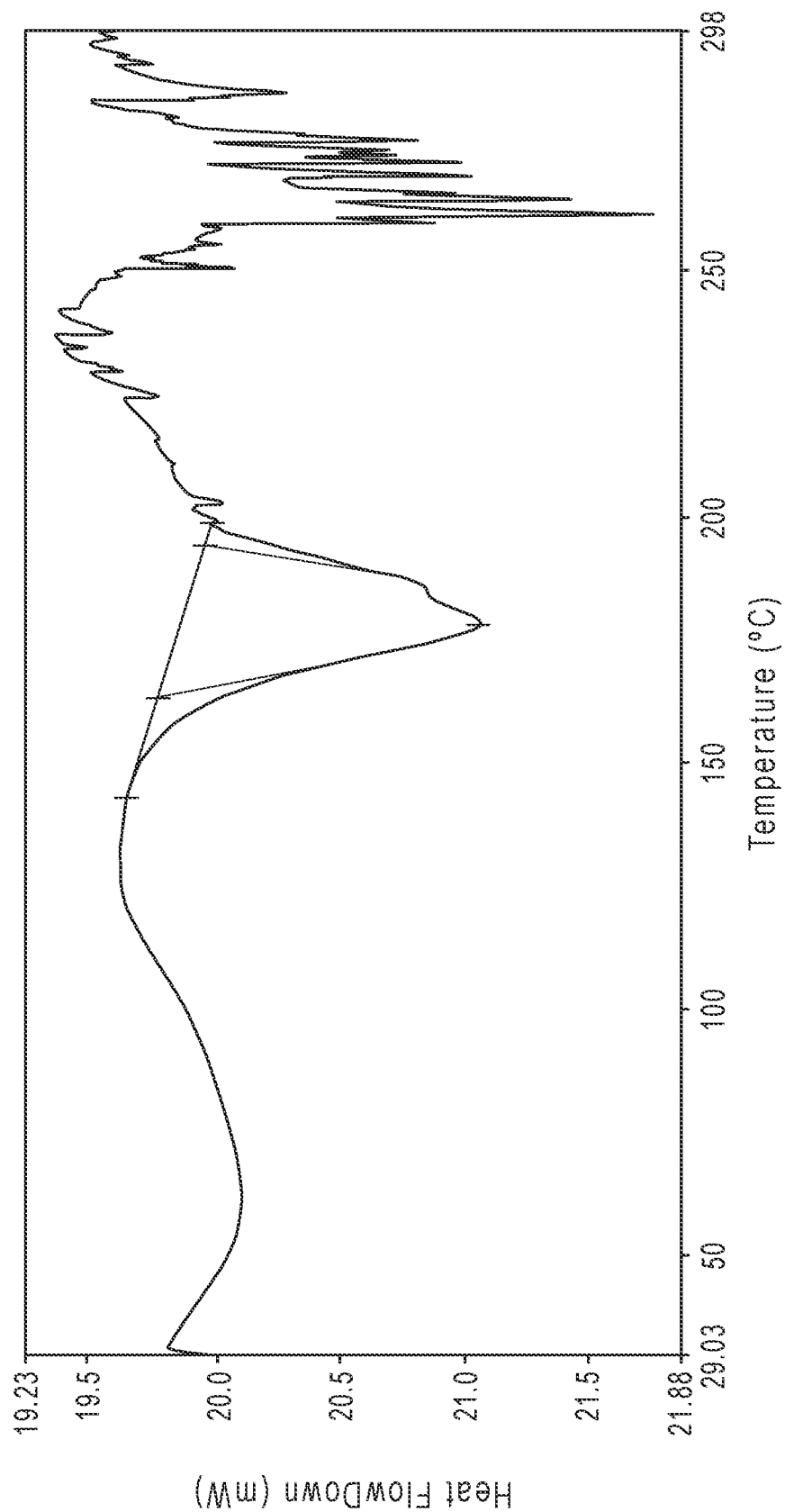
FIG. 8 shows a thermogravimetric analysis (TGA) scan of crystalline 5-(dimethylamino)-N-(4-(morpholinomethyl) phenyl)naphthalene-1-sulfonamide dihydrochloride monohydrate prepared by exposing crystalline anhydrous 5-(dimethylamino)-N-(4-(morpholinomethyl)phenyl) naphthalene-1-sulfonamide dihydrochloride to atmospheric moisture.

The dihydrochloride monohydrate salt can exhibit a differential scanning calorimetry curve as substantially shown in FIG. 8.

Compound (1) can be synthesized using methods known in the art.

Compound (1) can be prepared according to Scheme 5 as disclosed in paragraph [00277] of PCT International Publication No. PCT/US2019/064960 or as described in Example 1.

To prepare the dihydrochloride salt, 5-(dimethylamino)-N-(4-(morpholinomethyl)phenyl)naphthalene-1-sulfonamide (free base) can be reacted with hydrogen chloride in an organic solvent in methanol to provide 5-(dimethylamino)-N-(4-(morpholinomethyl)phenyl)naphthalene-1-sulfonamide dihydrochloride. To provide the dihydrochloride dihydrate salt, the dihydrochloride salt can be suspended in methanol (3.0 vol) and water (2.0 eq) and stirred for 1 h at 25° C. to 30° C. The solids can be filtered and washed with methanol (1.5 vol) to provide compound (1) with a water content of 6.2 mol %.

A pharmaceutical composition provided by the present disclosure can comprise compound (1).

A pharmaceutical composition can comprise a therapeutically effective amount of compound (1) for treating a disease in a patient.

A pharmaceutical composition can comprise one or more pharmaceutically acceptable carriers, excipients diluents, or combinations of any of the foregoing.

Compound (1) can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. Pharmaceutical compositions provided by the present disclosure can be injectable intravenous formulations. Pharmaceutical compositions provided by the present disclosure can be oral formulations. Oral formulations may be oral dosage forms. A pharmaceutical composition may be formulated for intravenous administration or for subcutaneous administration.

Pharmaceutical compositions provided by the present disclosure may comprise a therapeutically effective amount of compound (1) together with a suitable amount of one or more pharmaceutically acceptable vehicles so as to provide a composition for proper administration to a patient. Suitable pharmaceutical vehicles and methods of preparing pharmaceutical compositions are described in the art.

Following administration to a patient, compound (1) will dissociated to provide the parent compound, 5-(eimethylamino)-N-(4-(morpholinomethyl)phenyl)naphthalene-1-sulfonamide, compound (2).

A pharmaceutical composition provided by the present disclosure can be formulated for oral administration. A pharmaceutical composition formulated for oral administration can comprise any suitable oral dosage form including, for example, tablets, capsules, caplets, sachets, bottles, stick packs, dispersions, and suspensions.

A pharmaceutical composition formulated for oral administration can provide for a modified release profile in the gastrointestinal tract, such as a controlled release profile, a sustained release profile, a pH-release profile, a pulsatile release profile, a timed-release profile, or a delayed release profile. A pharmaceutical composition formulated for oral administration can be configured to release compound (1) over an intended period of time following ingestion and/or in an intended region of the gastrointestinal tract.

A pharmaceutical composition formulated for oral administration can provide for an immediate release profile.

Assessing single patient response to therapy and qualifying a patient for optimal therapy are among the greatest challenges of modern healthcare and relate to trends in personalized medicine. Compound (1) can have target selectivity, for example, for certain cancers and immune cells. Compound (1) radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using compound (1), once correlated to the concentration can provide a three-dimensional distribution map, which can then be used for macroscopic dose calculations.

Accordingly, it is within the capability of those of skill in the art to assay and use compound (1) and/or pharmaceutical compositions thereof for therapy.

Compound (1) and/or pharmaceutical composition thereof can generally be used in an amount effective to achieve the intended purpose. For use to treat a disease such as cancer, an autoimmune disease or an inflammatory disease, compound (1) can be administered or applied in a therapeutically effective amount.

The amount of compound (1) that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of compound (1) can depend on, among other factors, the patient being treated, the weight of the patient, the severity of the affliction, the manner of administration and the judgment of the prescribing physician.

Compound (1) can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

A therapeutically effective dose of compound (1) and/or pharmaceutical composition thereof will provide therapeutic benefit without causing substantial toxicity. Toxicity of a compound (1) and/or pharmaceutical composition thereof may be determined using standard pharmaceutical procedures and may be readily ascertained by the skilled artisan. The dose ratio between toxic and therapeutic effect is the therapeutic index. Compound (1) and/or pharmaceutical composition thereof exhibits a particularly high therapeutic index in treating disease and disorders. A dose of compound (1) and/or pharmaceutical composition thereof can be within a range of circulating concentrations that include an effective dose with minimal toxicity.

Compound (1) or a pharmaceutical composition thereof may be included in a kit that may be used to administer the compound to a patient for therapeutic purposes. A kit can include a pharmaceutical composition comprising compound (1) suitable for administration to a patient and instructions for administering the pharmaceutical composition to the patient. A kit can be suitable for treating cancer, for treating an autoimmune disease, or for treating an inflammatory disease. A kit can comprise compound (1), a pharmaceutically acceptable vehicle for administering the cocrystal, and instructions for administering the formulation comprising the cocrystal to a patient.

The pharmaceutical compositions can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compound (1) and pharmaceutical compositions comprising compound (1) can be used to treat a disease in which the etiology of the disease is associated with p38α MAPK protein activity.

Compound (1) dissociates in vivo to provide compound (2), which is a selective inhibitor of p38α MAPK. A selective p38α MAPK inhibitor has a higher binding affinity to the target pocket of p38α MAPK than to the catalytic binding site of p38α MAPK. A p38α MAPK inhibitor can bind to p38α MAPK near the substrate binding groove of p38α MAPK, which extends between two acidic regions, the CD and ED domains. The binding pocket can be defined at least by residues R49, H107, L108, and K165 of p38α MAPK. The binding pocket can be defined at least by residues R49, H107, L108, M109, G110, A157, V158, E163, L164, and K165 of p38α MAPK.

Selective binding of compound (2) p38α MAPK can be confirmed using complementary technologies. For example, a selective p38α MAPK inhibitor can show a concentration-dependent increase in melting temperature of p38α but not p38β as determined using DSF, which detects ligand-induced protein stabilization. STD-NMR, which measures low affinity protein/ligand binding via non-scalar magnetization transfer from protein to ligand protons, can be used to confirm specific compound binding to p38α and localized the interaction to its aromatic rings. A p38α MAPK inhibitor can cause a concentration-dependent increase in melting temperature of p38α MAPK. The difference in melting temperature Tm can be measured at a p38α MAPK inhibitor concentration of between 1 nM and 1000 μM such as at a concentration of 100 μM. For example, the difference in the melting temperature can be from 0.1° C. and about 2° C.

Compound (2) can interact with a pocket near the ED substrate docking site of p38 MAPK.

Compound (2) can bind to p38α MAPK near the substrate binding groove of p38α MAPK, which extends between the CD and ED domains.

Compound (2) can inhibit MK2 phosphorylation through interaction with p38α MAPK.

Compound (2) can competitively bind to p38α MAPK with 4-chloro-N-(4-((1,1-dioxidothiomorpholino)methyl)phenyl)benzamide.

Compound (2) can have a higher binding affinity to the p38α MAPK subunit than to the p38β MAPK subunit.

A p38α MAPK inhibitor can have a logP, for example, from -5 to 10, from -3 to 8, from 0 to 5, 0.1 to 3, from 0.1 to 1, from 0.5 to 1.5, from 0.75 to 2, from 1 to 2.5, or from 1.75 to 3. LogP is a measure of drug solubility and is defined as the logarithm of the octanol/water partition coefficient of the drug.

Phosphorylation of MK2 requires binding to the ED site adjacent to the target pocket in p38α MAPK. The target pocket can be defined by amino acids R49, H107, L108, and K165 in p38α MAPK. The target pocket can be defined by amino acids selected from R49, H107, L108, M109, G110, A157, V158, E163, L164, and K165 in p38α MAPK. The target pocket can be defined by the amino acids R49, H107, L108, M109, G110, A157, V158, E163, L164, and K165 in p38α MAPK.

Compound (2) can at least partially inhibit MK2 phosphorylation. For example, Western blotting can be used to measure inhibition of MK2 phosphorylation in anisomycin-stimulated HeLa cells by compound (2).

Compound (2) can stabilize an endothelial or epithelial barrier function. Endothelial barrier permeability can be measured by separate or combined exposure to TNFa and hyperthermia, followed by measurement of permeably for 10 kDa dextran. For example, endothelial barrier stabilization can be assessed by pretreating with compound (2), preceded and followed by permeability measurements, where stabilization can be expressed as a percent reduction in the before and after pretreatment permeability increase. A permeability increase for 10 kDa dextran can be reduced by between 5% to more than 100% such as, for example, by greater than 5%, greater than 10%, greater than 20%, greeter than 40%, greater than 60%, greater than 80%, or greater than 100%.

Compound (2) can modulate TNFa-induced gene expression in human lung microvascular endothelial cells (HMVECLs) as determined using, for example, RNASeq. For example, HMVECLs can be pretreated for a period of time with a p38α MAPK inhibitor at an appropriate concentration and then stimulated with TNFa for a period of time. Compound (1) can inhibit genes such as PRRG4, TSLP, CCLI7, EXOC3L4, MMP9, IDOI, CXCL1O, CD200, SLCI5A3, VDR, ILIB, GPR88, CD207, TCHH, HAS3, GBPIPI, MUC4, ELOVL7, CXCL11, GBP4, PLAIA, and/or CXCLS.

The effects of a p38α MAPK inhibitor on inflammatory cytokine expression can be determined by pretreating PMA-differentiated THPI cells with a p38α MAPK inhibitor, then stimulating with LPS, and harvesting RNA a period of time later for analysis by PCR-based cytokine array. A p38α MAPK inhibitor can inhibit expression of various genes, such as IL-IA, IL-8, TNFSF8, CXCLS, CCL7, CCLI7, TNFSF9, IL-IB, CXCLI, TNFSFIS, CCLS, CCL4, CCL20, CXCL2, TNF, or BMP6. A p38α MAPK inhibitor can inhibit expression of Smad3, which drives differentiation of Foxp3 T regulatory cells and suppresses interferon-y. Inflammation reduction can be measured by comparing the fold change mRNA levels vs. unstimulated PMA-differentiated THPI cells at various concentrations of p38α MAPK inhibitor.

Compound (1) or a pharmaceutical composition thereof can be used to treat a disease in a patient.

Compound (1) or a pharmaceutical composition thereof can be used to treat a disease in which the etiology of the disease is associated with up-regulation and/or down-regulation of the p38α MAPK protein.

Methods provided by the present disclosure include treating a disease in a patient comprising administering to a patient in need of such treatment a therapeutically effective amount of compound (1) or a pharmaceutical composition thereof, wherein the disease is treated by inhibiting the p38α MAPK protein.

The p38 mitogen-activated protein kinase (MAPK) family of stress- and cytokine-activated kinases are associated with the pathogenesis of many human diseases, including, for example, cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by p38 MAPK, regulation of endothelial and epithelial barrier function, leukocyte trafficking, and cytokine expression are central to the pathogenesis of acute and chronic inflammatory disorders.

Compound (1) or a pharmaceutical composition thereof can be used for treating cancer in a patient. The cancer can be, for example, a solid tumor or a metastasis.

Methods provided by the present disclosure include methods of treating cancer in a patient comprising administering to a patient in need of such treatment a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma, and the like. In other embodiments, the cancer is acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliosarcoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendothelioma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom macroglobulinemia.

Compound (1) or a pharmaceutical composition thereof can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenstrom macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need of such treatment a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephrits, atherosclerosis/acute coronary syndrome, chronic obstructive pulmonary disease, asthma, inflammatory bowel disease, Crohn's disease, psoriasis, lupus, multiple sclerosis, inflammation in hypoercholesteremia, pain, diabetes, and rheumatoid arthritis.

Methods provided by the present disclosure include methods of treating an autoimmune disease in a patient comprising administering to a patient in need of such treatment a therapeutically effective amount of a compound or pharmaceutical composition provided by the present disclosure.

Compound (1) or a pharmaceutical composition thereof can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases,* Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Behcet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto's thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

Compound (1) or a pharmaceutical composition thereof can be used to treat autoimmune disorders such as, for example, lupus, graft-versus-host disease, hepatitis C-induced vasculitis, Type I diabetes, multiple sclerosis, spontaneous loss of pregnancy, atopic diseases, and inflammatory bowel diseases.

Compound (1) or a pharmaceutical composition thereof can be administered with one or more additional therapeutic agents for treating an autoimmune disease. Compound (1) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need of such treatment a therapeutically effective amount of compound (1), wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis. Compound (1) or a pharmaceutical composition thereof can be administered to a patient to treat a symptom of a viral infection such as a COVID19 infection.

Methods provided by the present disclosure include methods of treating a disease in a patient comprising administering to a patient in need of such treatment a therapeutically effective amount of compound (1), wherein the disease is a respiratory disease.

Methods provided by the present disclosure include methods of treating a disease in a patient comprising administering to a patient in need of such treatment a therapeutically effective amount of a compound or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need of such treatment a therapeutically effective amount of compound (1) or a pharmaceutical composition of such treatment, wherein the disease is selected from sudden idiopathic hearing loss, drug induced hearing loss, age-related hearing loss, and Duchenne muscular dystrophy.

The amount of compound (1), or pharmaceutical composition thereof that will be effective in the treatment of a cancer can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a compound (1) administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound (1) and appropriate dosing intervals may be selected to maintain a sustained therapeutically effective concentration of compound (2) in the blood of a patient, and in certain embodiments, without exceeding a minimum adverse concentration.

A pharmaceutical composition comprising compound (1) may be administered, for example, 4 time per day, twice a day, once a day, once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound (1) contained within each of the multiple dosage forms may be the same or different.

Suitable daily dosage ranges for administration can range, for example, from about 2µg to about 200 mg of compound (1) per kilogram body weight.

Suitable daily dosage ranges for administration may range, for example, from about 1µg to about 50 mg of compound (1) per square meter ($m^2$) of body surface.

Compound (1) may be administered to treat cancer in a patient in an amount, for example, from 0.001 mg/day to 100 mg/day, or in any other appropriate daily dose. A dose can be, for example, from 0.01 µg/kg body weight/week to 100 µg/kg body weight/week or any other suitable dose.

A pharmaceutical composition comprising compound (1) may be administered to treat cancer in a patient so as to provide a therapeutically effective concentration of compound (2) in the blood or plasma of the patient. A therapeutically effective concentration of a compound of compound (1) in the blood of a patient can be, for example, from 0.01 µg/L to 1,000 µg/L, from 0.1 µg/L to 500 µg/L, from 1 µg/L to 250 µg/L, or from about 10 µg/L to about 100 µg/L. A therapeutically effective concentration of compound (2) in the blood of a patient can be, for example, at least 0.01 µg/L, at least 0.1 µg/L, at least 1 µg/L, at least about 10 µg/L, or at least 100 µg/L. A therapeutically effective concentration of a compound (2) in the blood of a patient can be, for example, less than an amount that causes unacceptable adverse effects including adverse effects to homeostasis. A therapeutically effective concentration of compound (2) in the blood of a patient can be an amount sufficient to restore and/or maintain homeostasis in the patient.

Pharmaceutical compositions provided by the present disclosure may be administered to treat a disease in a patient so as to provide a therapeutically effective concentration of compound (2) in the blood of a patient for a period of time such as, for example, for 4 hours, 8 hours, 12 hours, 16 hours, 20 hours, 1 day, or 2 days.

The amount of compound (1) administered may vary during a treatment regimen.

Pharmaceutical compositions provided by the present disclosure may further comprise one or more pharmaceutically active compounds in addition to compound (1). Such compounds may be provided, for example, to treat the cancer being treated with compound (2) or to treat a disease, disorder, or condition other than the cancer being treated with compound (2), to treat a side-effect caused by compound (2), to augment the efficacy of compound (2), and/or to modulate the activity of compound (2).

Compound (1) may be administered in combination with at least one other therapeutic agent. Compound (1) may be administered to a patient together with another compound for treating cancer in the patient. Compound (1) and the at least one other therapeutic agent may act additively or, and in certain embodiments, synergistically. The at least one additional therapeutic agent may be included in the same pharmaceutical composition or vehicle comprising compound (1) or may be in a separate pharmaceutical composition or vehicle. Accordingly, methods provided by the present disclosure further include, in addition to administering compound (1), administering one or more therapeutic agents effective for treating cancer or a different disease, disorder or condition than cancer. Methods provided by the present disclosure include administering compound (1) and one or more other therapeutic agents provided that the combined administration does not inhibit the therapeutic efficacy of compound (2) and/or does not produce adverse combination effects.

A pharmaceutical composition comprising compound (1) may be administered concurrently with the administration of another therapeutic agent, which may be part of the same pharmaceutical composition as, or in a different pharmaceutical composition than that comprising compound (1). Compound (1) may be administered prior or subsequent to administration of another therapeutic agent. In certain combination therapies, the combination therapy may comprise alternating between administering compound (1) and a composition comprising another therapeutic agent, e.g., to minimize adverse drug effects associated with a particular drug. When compound (1) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising compound (1) may be administered with one or more substances, for example, to enhance, modulate and/or control release, bioavailability, therapeutic efficacy, therapeutic potency, and/or stability, of compound (1) and/or compound (2). For example, a pharmaceutical composition comprising compound (1) can be co-administered with an active agent having pharmacological effects that enhance the therapeutic efficacy of compound (2).

Compound (1) or a pharmaceutical composition thereof may be administered in conjunction with an agent known or believed to be effective in treating a disease such as cancer, an autoimmune disease or an inflammatory disease in a patient, such as the same disease being treated with compound (1).

Compound (1) or a pharmaceutical composition thereof may be administered in conjunction with an agent known or believed to interfere with cell proliferation.

Compound (1) or a pharmaceutical composition thereof may be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

Compound (1) or a pharmaceutical composition thereof may be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. Compound (1) or a pharmaceutical composition thereof may be administered in conjunction with an immunomodulator such as CD137/4-1BB, CD27, GIYR, and/or OC40.

Compound (1) or a pharmaceutical composition thereof may be administered in conjunction with an agent known or believed to be cytotoxic, to cause DNA damage, to cause cell cycle arrest, or to cause mitotic catastrophe.

Compound (1) or a pharmaceutical composition thereof may be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

Compound (1) or a pharmaceutical composition thereof may be administered in conjunction with an agent known or believed to interfere with neovascularization, to reduce neovascularization, or to promote neovascularization.

Compound (1) or a pharmaceutical composition thereof may be administered in conjunction with an agent known or believed to interfere with hormone homeostasis, to interfere with hormone synthesis, to interfere with hormone receptor binding, or to interfere with hormone signal transduction.

Compound (1) or a pharmaceutical composition thereof may be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

Compound (1) or a pharmaceutical composition thereof may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (Janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region—Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-a) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy)

sensitizer, an ATR (ataxia telangiectasia- and Rad3-related protein kinase) inhibitor, or a combination of any of the foregoing.

Compound (1) or a pharmaceutical composition thereof may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI 1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-059; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

Compound (1) or a pharmaceutical composition thereof may be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoximine, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

Compound (1) or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

Compound (1) or a pharmaceutical composition thereof may be co-administered with a compound that inhibits DNA repair such as, for example, O6-benzylguanine (O6-BG).

Compound (1) or a pharmaceutical composition thereof may be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, O6-benzylguanine, bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

A compound of Formula (1) or a pharmaceutical composition thereof may be administered in conjunction with one or more chemotherapeutic agents such as, for example, abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase erwinia chrysanthemi, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPDX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin a, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin hydrochloride, EPOCH, epoetin α, erdafitinib, eribulin mesylate, erlotinib hydrochloride, etoposide, etoposide phosphate, everolimus, exemestane, fec, filgrastim, fludarabine phosphate, fluorouracil injection, fluorouracil—topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, interferon α-2b recombinant, iobenguane $^{131}$I, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R-CHOP, R-CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and combinations of any of the foregoing.

The efficacy of administering compound (1) or a pharmaceutical composition thereof for treating cancer, an inflammatory disease, or an autoimmune disease. may be assessed using in vitro and animal studies and in clinical trials.

Methods of inhibiting p38α MAPK provided by the present disclosure include contacting p38α MAPK with a compound provided by the present disclosure to a pocket near the ED substrate-docking site of p38α MAPK.

Methods of inhibiting p38α MAPK provided by the present disclosure do not result in loss of p38α-dependent counterregulatory responses. The p38α-dependent counterregulatory response relates to mitogen- and stress-activated protein kinase-I (MSK1), or MSK2. In targeting a pocket near the ED substrate-docking site of p38α, the inhibitors provided by the present disclosure avoid interfering with CD-specific substrates, including MSK$^{1}/_{2}$, thus limiting inflammation through expression of IL-10 and DUSP2.

ASPECTS OF THE INVENTION

The invention is further defined by the following aspects.

Aspect 1. A compound, crystalline 5-(dimethylamino)-N-(4-(morpholinomethyl)phenyl)naphthalene-1-sulfonamide dihydrochloride dihydrate:

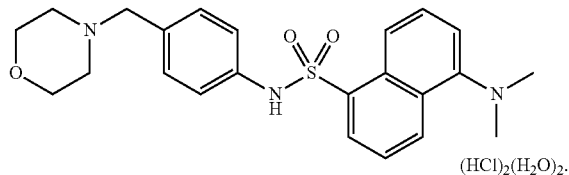 [SMILES: CN(C)c1cccc2c(S(=O)(=O)Nc3ccc(CN4CCOCC4)cc3)cccc12]

(HCl)$_2$(H$_2$O)$_2$.

Aspect 2. The compound of aspect 1, wherein the compound is characterized by an XRPD pattern comprising characteristic diffraction peaks at least at 10.5°±0.2°, 13.9°±0.2°, 14.8°±0.2°, 17.2°±0.2°, 20.4±0.2°, 22.6±0.2°, 25.7±0.2°, and 27.9±0.2° expressed as 2θ angles and determined using Cu-Kα radiation.

Aspect 3. The compound of aspect 1, wherein the compound is characterized by an XRPD pattern comprising characteristic diffraction peaks at least at 10.5°±0.1°, 13.9°±0.1°, 14.8°±0.1°, 17.2°±0.1°, 20.4±0.1°, 22.6±0.1°, 25.7±0.1°, and 27.9±0.2° expressed as 2θ angles and determined using Cu-Kα radiation.

Aspect 4. The compound of aspect 1, wherein the compound is characterized by an XRPD pattern comprising characteristic diffraction peaks at least at 7.5±0.2°, 8.5±0.2°, 10.5°±0.2°, 12.8±0.2°, 13.9°±0.2°, 14.8°±0.2°, 15.5±0.2°, 17.2±0.2°, 18.2±0.2°, 20.1±0.2°, 20.4±0.2°, 21.1±0.2°, 22.6±0.2°, 22.9±0.2°, 23.5±0.2°, 23.8±0.2°, 24.6±0.2°, 25.7±0.2°, 26.1±0.2°, 26.4±0.2°, 27.1±0.2°, 27.5±0.2°, 27.9±0.2°, and 32.4±0.2° expressed as 2θ angles and determined using Cu-Kα radiation.

Aspect 5. The compound of aspect 1, wherein the compound is characterized by an XRPD pattern comprising characteristic diffraction peaks at least at 7.5±0.1°, 8.5±0.1°, 10.5°±0.1°, 12.8±0.1°, 13.9°±0.1°, 14.8°±0.1°, 15.5±0.1°, 17.2±0.1°, 18.2±0.1°, 20.1±0.1°, 20.4±0.1°, 21.1±0.1°, 22.6±0.1°, 22.9±0.1°, 23.5±0.1°, 23.8±0.1°, 24.6±0.1°, 25.7±0.1°, 26.1±0.1°, 26.4±0.1°, 27.1±0.1°, 27.5±0.1°, 27.9±0.1°, and 32.4±0.1° expressed as 2θ angles and determined using Cu-Kα radiation.

Aspect 6. The compound of any one of aspects 1 to 5, wherein the compound is characterized by an XRPD pattern as substantially shown in FIG. 1.

Aspect 7. The compound of any one of aspects 1 to 6, wherein the compound has a melting onset temperature, for example, from 161° C. to 167° C., where the melting onset temperature is determined by differential scanning calorimetry.

Aspect 8. The compound of any one of aspects 1 to 6, wherein the compound has a melting onset temperature, for example, of 164.3° C.±0.5° C., where the melting onset temperature is determined by differential scanning calorimetry.

Aspect 9. The compound of any one of aspects 1 to 8, wherein the compound has a melting enthalpy, for example, from 89 J/g to 99 J/g, where the melting enthalpy is determined by differential scanning calorimetry.

Aspect 10. The compound of any one of aspects 1 to 8, wherein the compound has a melting enthalpy, for example, of 94.25 J/g±0.5 J/g, where the melting enthalpy is determined by differential scanning calorimetry.

Aspect 11. The compound of any one of aspects 1 to 10, wherein the compound has a melting peak, for example, from 178.5 J/g to 184.5 J/g, where the melting peak is determined by differential scanning calorimetry.

Aspect 12. The compound of any one of aspects 1 to 10, wherein the compound has a melting peak, for example, at 181.6° C.±2.0° C., where the melting peak is determined by differential scanning calorimetry.

Aspect 13. The compound of any one of aspects 1 to 12, wherein the compound exhibits a differential scanning calorimetry curve as substantially shown in FIG. 2.

Aspect 14. The compound of any one of aspects 1 to 13, wherein the compound has a weight loss, for example, from 13% to 15% at a temperature from 25° C. to 210° C., where the weight loss is determined by thermogravimetric analysis at a scan rate of 2° C./min.

Aspect 15. The compound of any one of aspects 1 to 13, wherein the compound has a weight loss, for example, of 13.9%±1.0% at a temperature from 25° C. to 210° C., where the weight loss is determined by thermogravimetric analysis at a scan rate of 2° C./min.

Aspect 16. The compound of any one of aspects 1 to 15, wherein the compound exhibits a differential thermal calorimetry curve as substantially shown in FIG. 3.

Aspect 17. The compound of any one of aspects 1 to 16, wherein the compound has a weight loss, for example, from 2% to 6% at a temperature from 25° C. to 122° C., where the weight loss is determined by thermogravimetric analysis at a scan rate of 4.25° C./min.

Aspect 18. The compound of any one of aspects 1 to 16, wherein the compound has a weight loss, for example, of 4.25%±1.0% at a temperature from 25° C. to 122° C., where the weight loss is determined by thermogravimetric analysis at a scan rate of 4.25° C./min.

Aspect 19. The compound of any one of aspects 1 to 16, wherein the compound exhibits a differential thermal calorimetry curve as substantially shown in FIG. 4.

Aspect 20. A pharmaceutical composition comprising the compound of any one of aspects 1 to 19.

Aspect 21. The pharmaceutical composition of any one of aspects 1 to 19, wherein the pharmaceutical composition comprises a therapeutically effective amount of the compound for treating a disease in a patient.

Aspect 22. The pharmaceutical composition of aspect 21, wherein the disease is treated by inhibiting the p38α MAPK receptor.

Aspect 23. The pharmaceutical composition of aspect 21, wherein the disease is cancer.

Aspect 24. The pharmaceutical composition of aspect 21, wherein the disease is an inflammatory disease.

Aspect 25. The pharmaceutical composition of aspect 21, wherein the disease is an autoimmune disease.

Aspect 26. The pharmaceutical composition of aspect 21, wherein the disease is selected from acute lung injury, acute respiratory distress syndrome (ARDS), and chronic obstructive pulmonary disease (COPD).

Aspect 27. A method of treating a disease in a patient comprising administering to a patient in need of such treatment a therapeutically effective of amount of the compound of any one of aspects 1 to 19, wherein the disease is treated by inhibiting the p38α MAPK receptor.

Aspect 28. A method of treating a disease in a patient comprising administering to a patient in need of such treatment a therapeutically effective of amount of the compound of any one of aspects 1 to 19, wherein the disease is cancer.

Aspect 29. The method of aspect 28, wherein the cancer is selected from breast cancer and melanoma.

Aspect 30. A method of treating a disease in a patient comprising administering to a patient in need of such treatment a therapeutically effective of amount of the compound of any one of aspects 1 to 19, wherein the disease is an inflammatory disease.

Aspect 31. The method of aspect 30, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 32. A method of treating a disease in a patient comprising administering to a patient in need of such treatment a therapeutically effective of amount of the compound of any one of aspects 1 to 19, wherein the disease is an autoimmune disease.

Aspect 33. A method of treating a disease in a patient comprising administering to a patient in need of such treatment a therapeutically effective of amount of the compound of any one of aspects 1 to 19, wherein the disease is an age-related disease.

Aspect 34. The method of aspect 33, wherein the age-related disease is selected from hearing loss, muscle degeneration, Werner's syndrome, cellular aging, and Alzheimer's disease.

Aspect 35. A method of treating a disease in a patient comprising administering to a patient in need of such treatment a therapeutically effective of amount of the compound of any one of aspects 1 to 19, wherein the disease is selected from acute lung injury, acute respiratory distress syndrome (ARDS), and chronic obstructive pulmonary disease (COPD).

Aspect 36. A method of inhibiting the p38α MAPK receptor comprising contacting the p38α MAPK receptor with the compound of any one of aspects 1 to 19.

Aspect 37. A method of inhibiting the p38α MAPK receptor in a patient comprising administering to a patient a pharmacologically effective amount of the compound of any one of aspects 1 to 19.

Aspect 38. The method of aspect 37, wherein inhibiting the p38α MAPK receptor comprises selectively inhibiting the p38α MAPK receptor.

Aspect 39. The method of aspect 38, wherein inhibiting the p38α MAPK receptor does not result in loss of a p38α-dependent counterregulatory response.

Aspect 40. The method of aspect 39, wherein the p38α-dependent counterregulatory response relates to mitogen- and stress-activated protein kinase-1 (MSK1) or MSK2.

Aspect 41. The method of any one of aspects 37 to 40, wherein inhibiting the p38α MAPK receptor stabilizes an endothelial or epithelial barrier function.

Aspect 42. The method of any one of aspects 37 to 41, wherein inhibiting the p38α MAPK receptor reduces inflammation.

Aspect 43. The method of any one of aspects 37 to 42, wherein inhibiting the p38α MAPK receptor mitigates KPS-induced lung injury.

Aspect 44. The method of any one of aspects 37 to 43, wherein inhibiting the p38α MAPK receptor regulates leukocyte trafficking.

Aspect 45. The method of any one of aspects 37 to 44, wherein inhibiting the p38α MAPK receptor regulates cytokine expression.

EXAMPLES

The following examples describe in detail methods of preparing crystalline 5-(dimethylamino)-N-(4-(morpholinomethyl)phenyl)naphthalene-1-sulfonamide dihydrochloride dihydrate salt, properties of the crystalline salt, and methods of using the crystalline salt provided by the present disclosure. It will be apparent to those skilled in the art that many modifications, both to materials and methods, may be practiced without departing from the scope of the invention.

Example 1

Preparation of Compound (1)

Compound (1) was prepared according to Scheme 5 as disclosed in paragraph [00277] of PCT International Publication No. PCT/US2019/064960.

4-Nitrobenzyl chloride (1.0 eq) was added in isopropanol (5.0 vol) under an inert atmosphere at 25° C. to 30° C. The solution was stirred for 15 min and 2.1 eq morpholine was slowly added while maintaining the temperature at 25° C. to 30° C. The mixture was heated to 65° C. and the progress of the reaction monitored by TLC/HPLC. The reaction to provide 4-(4-nitrobenzyl)morpholine was complete after 3 hours.

4-(4-Nitrobenzyl)morpholine in methanol was exposed to Raney Ni at 65° C. to provide 4-(morpholinomethyl)aniline.

4-(Morpholinomethyl)aniline and 5-(dimethylamino)naphthalene-1-sulfonyl chloride were reacted with dansyl chloride in the presence of a tertiary amine base such as N-methylmorpholine in dichloromethane to provide 5-(dimethylamino)-N-(4-(morpholinomethyl)phenyl)naphthalene-1-sulfonamide.

5-(Dimethylamino)-N-(4-(morpholinomethyl)phenyl)naphthalene-1-sulfonamide was reacted with 4M HCl in 1,4-dioxane in methanol at a temperature from 0° C. to 25° C. to provide 5-(dimethylamino)-N-(4-(morpholinomethyl)phenyl)naphthalene-1-sulfonamide dihydrochloride.

The dihydrochloride (1 eq) was suspended in methanol (3 vol) and water (2 eq) and the suspension was stirred for 1 hour at 20° C. to 30° C. to provide crystalline 5-(dimethylamino)-N-(4-(morpholinomethyl)phenyl)naphthalene-1-sulfonamide dihydrochloride dihydrate. The solids were filtered and washed with methanol (1.5 vol).

Figure 9:
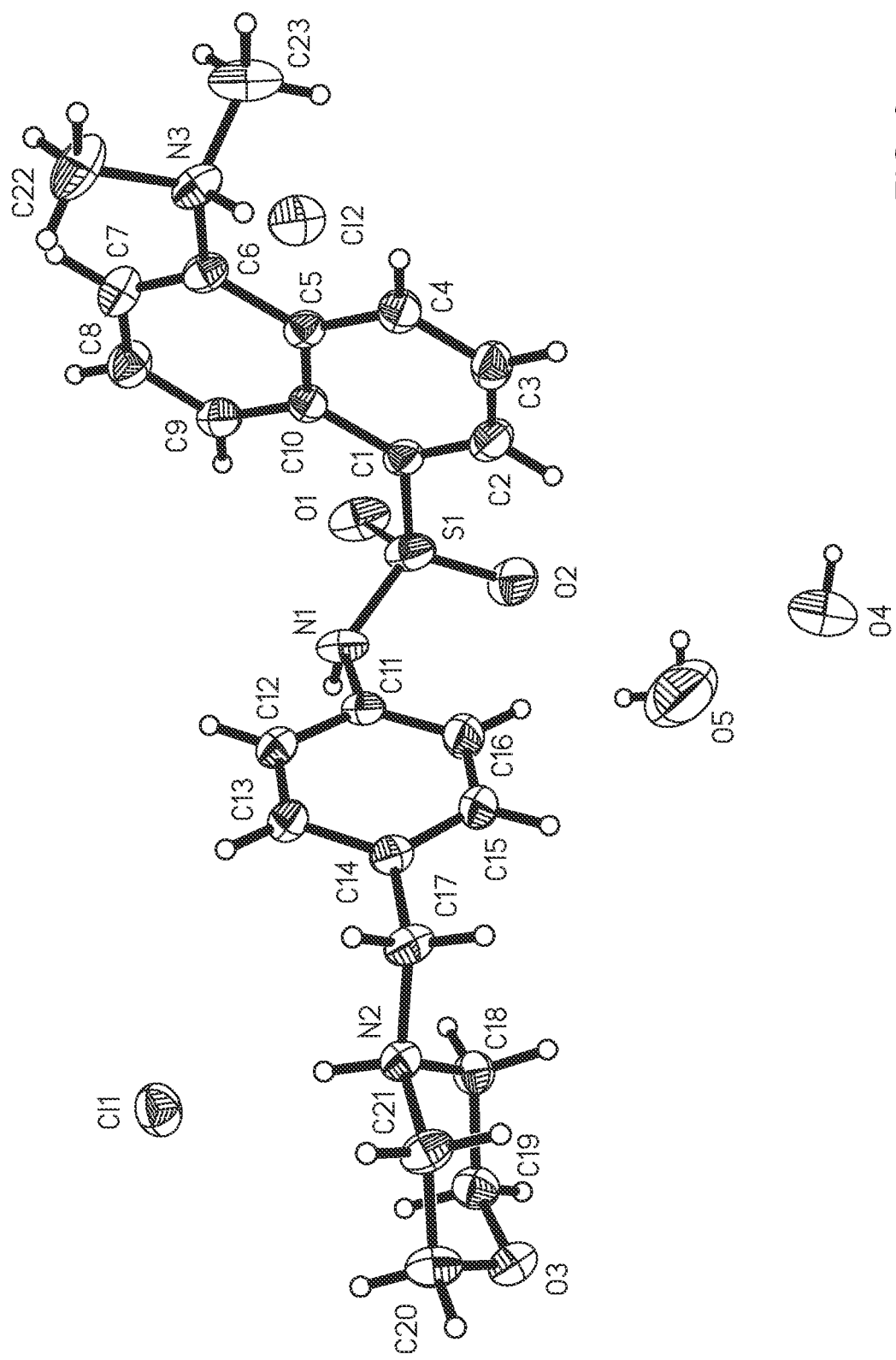
FIGS. 9 and 10 show the three-dimensional crystal structure of crystalline 5-(dimethylamino)-N-(4-(morpholinomethyl)phenyl)naphthalene-1-sulfonamide dihydrochloride dihydrate.
Figure 10:
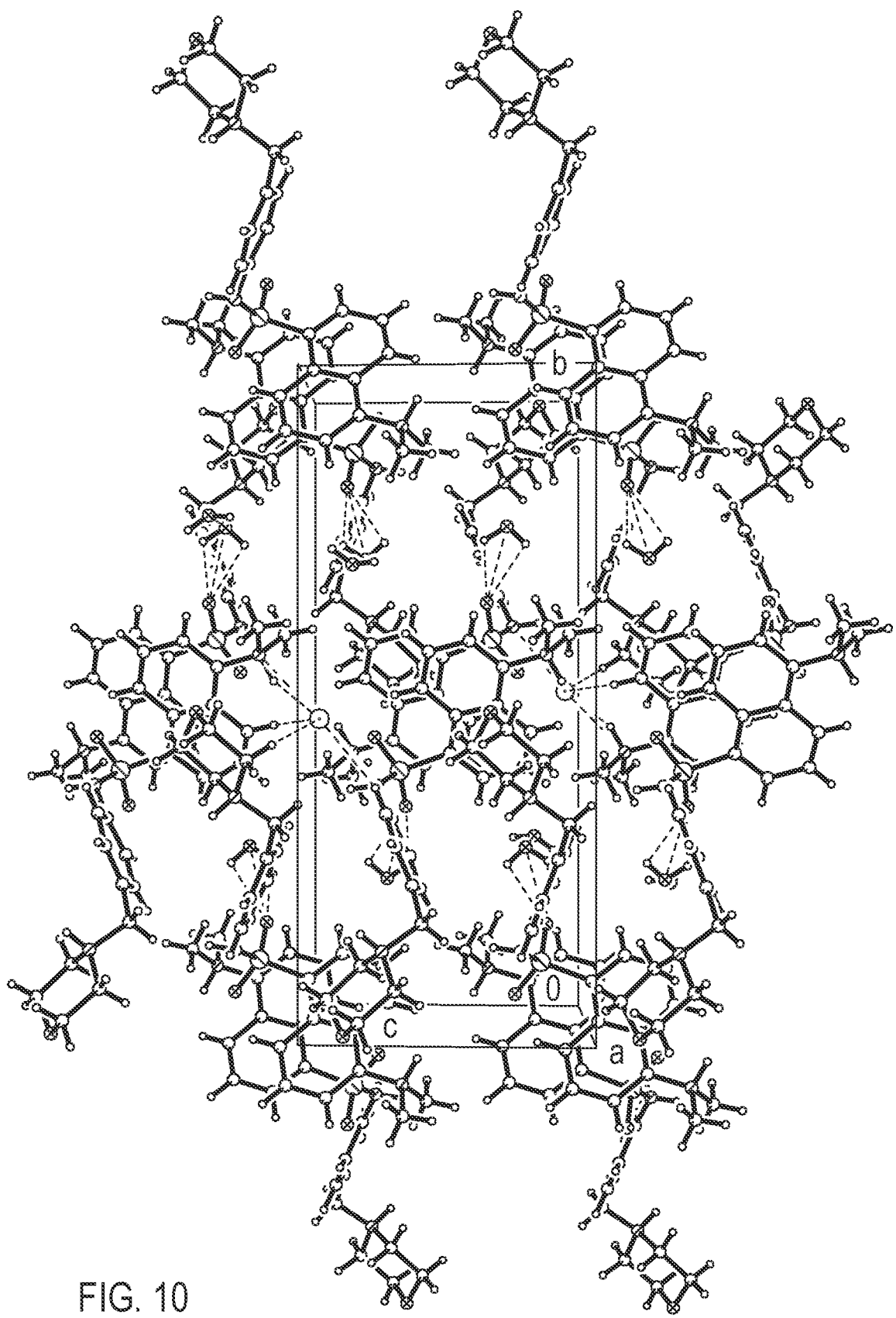

X-ray powder diffraction (XRPD) was performed using a Shimadzu Lab XRD-6100 instrument with a scintillation detector in continuous scan mode using a Cu/K-α (λ=1.5418 Å) source. The diffraction patterns were obtained over a scan range from 3° to 50° at a scan speed of 2 deg/min, a sampling pitch of 0.02 deg and a preset time of 0.6 sec. The method was used to obtain the XRPD patterns presented inf FIGS. 1, 5, and 7, and the data was used to derive the crystal structures presented in FIGS. 9-10.

Differential scanning calorimetry (DSC) was performed using a Perkin Elmer DSC 4000 (version 13.2.1.0007) instrument over a temperature range from 30° C. to 300° C. at a heating rate of 5° C./min and a nitrogen flow rate of 80 mL/min, using a sample mass from 3 mg to 4 mg. The method was used to obtain the DSC curves presented in FIGS. 4 and 6.

Differential thermogravimetric analysis (TGA) was performed using a Shimadzu DTG-60 instrument over a temperature range from less than 25° C. to 400° C. at a heating rate of 2° C./min using a sample mass of 10 mg. The method was used to provide the TGA curves presented in FIGS. 2 and 3.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound, crystalline 5-(dimethylamino)-N-(4-(morpholinomethyl)phenyl)naphthalene-1-sulfonamide:

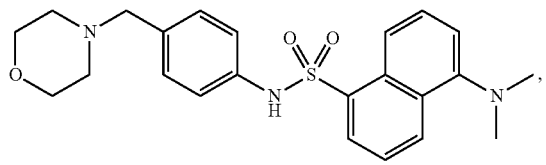 [SMILES: CN(C)c1cccc2c(S(=O)(=O)Nc3ccc(CN4CCOCC4)cc3)cccc12]

wherein the compound is characterized by an X-ray powder diffraction (XRPD) pattern comprising characteristic diffraction peaks at least at 13.1°±0.2°, 14.6°±0.2°, 15.0°±0.2°, 18.1°±0.2°, 22.2°±0.2°, 22.6°±0.2°, and 24.4°±0.2° expressed as 2θ angles and determined using Cu-Kα radiation.

2. The compound of claim 1, wherein the compound is characterized by an XRPD pattern comprising characteristic diffraction peaks at least at 13.1°±0.1°, 14.6°±0.1°, 15.0°±0.1°, 18.1°±0.1°, 22.2°±0.1°, 22.6°±0.1°, and 24.4°±0.1° expressed as 2θ angles and determined using Cu-Kα radiation.

3. The compound of claim 1, wherein the compound is characterized by an XRPD pattern as shown in FIG. 5.

4. The compound of claim 1, wherein the compound has a primary melting onset temperature from 158° C. to 164° C., and wherein the primary melting onset temperature is determined by differential scanning calorimetry.

5. The compound of claim 1, wherein the compound has a primary melting enthalpy from 60 J/g to 65 J/g, and wherein the primary melting enthalpy is determined by differential scanning calorimetry.

6. The compound of claim 1, wherein the compound has a primary melting peak from 175 J/g to 182 J/g, and wherein the primary melting peak is determined by differential scanning calorimetry.

7. The compound of claim 1, wherein the compound has a secondary melting onset temperature of 204.7° C., a secondary melting enthalpy of 20.7 J/g, and a secondary melting peak at 211.2° C.

8. The compound of claim 1, wherein the compound exhibits a differential scanning calorimetry curve as shown in FIG. 6.

9. A pharmaceutical composition comprising the compound of claim 1.

10. The pharmaceutical composition of claim 9, wherein the pharmaceutical composition comprises a therapeutically effective amount of the compound for treating a disease in a patient, wherein the disease is selected from cancer, an inflammatory disease, and an autoimmune disease.

11. A method of treating a disease in a patient comprising administering to a patient in need of such treatment a therapeutically effective of amount of the pharmaceutical composition of claim 9, wherein the disease is selected from breast cancer and melanoma.

12. A method of treating a disease in a patient comprising administering to a patient in need of such treatment a therapeutically effective of amount of the pharmaceutical composition of claim 9, wherein the disease is an inflammatory disease, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

13. A method of treating a disease in a patient comprising administering to a patient in need of such treatment a therapeutically effective of amount of the pharmaceutical composition of claim 9, wherein the disease is an autoimmune disease, wherein the autoimmune disease is selected from segmental glomerulonephritis, asthma, inflammatory disease, Crohn's disease, psoriasis, lupus, multiple sclerosis, pain, diabetes and rheumatoid arthritis.

14. A method of treating a disease in a patient comprising administering to a patient in need of such treatment a therapeutically effective of amount of the pharmaceutical composition of claim 9, wherein the disease is an age-related disease, wherein the age-related disease is selected from hearing loss, muscle degeneration, Werner's syndrome, cellular aging, and Alzheimer's disease.

15. A method of treating a disease in a patient comprising administering to a patient in need of such treatment a therapeutically effective of amount of the pharmaceutical composition of claim 9, wherein the disease is selected from acute lung injury, acute respiratory distress syndrome (ARDS), and chronic obstructive pulmonary disease (COPD).

16. A method of treating a disease in a patient comprising administering to a patient in need of such treatment a therapeutically effective of amount of the compound of claim 1, wherein the disease is selected from breast cancer and melanoma.

17. A method of treating a disease in a patient comprising administering to a patient in need of such treatment a therapeutically effective of amount of the compound of claim 1, wherein the disease is an inflammatory disease, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

18. A method of treating a disease in a patient comprising administering to a patient in need of such treatment a therapeutically effective of amount of the compound of claim 1, wherein the disease is an autoimmune disease, wherein the autoimmune disease is selected from segmental glomerulonephritis, asthma, inflammatory disease, Crohn's disease, psoriasis, lupus, multiple sclerosis, pain, diabetes and rheumatoid arthritis.

19. A method of treating a disease in a patient comprising administering to a patient in need of such treatment a therapeutically effective of amount of the compound of claim 1, wherein the disease is an age-related disease, wherein the age-related disease is selected from hearing loss, muscle degeneration, Werner's syndrome, cellular aging, and Alzheimer's disease.

20. A method of treating a disease in a patient comprising administering to a patient in need of such treatment a therapeutically effective of amount of the compound of claim 1, wherein the disease is selected from acute lung injury, acute respiratory distress syndrome (ARDS), and chronic obstructive pulmonary disease (COPD).

\* \* \* \* \*

UNITED STATES PATENT AND TRADEMARK OFFICE
CERTIFICATE OF CORRECTION

| | | |
|---|---|---|
| PATENT NO. | : 12,269,792 B2 | Page 1 of 1 |
| APPLICATION NO. | : 17/743035 | |
| DATED | : April 8, 2025 | |
| INVENTOR(S) | : Adam Galan, Ritu Lal and Wendy Luo | |

It is certified that error appears in the above-identified patent and that said Letters Patent is hereby corrected as shown below:

On the Title Page

Item (73) the Assignee, that reads "GENIE LIFESCIENCES INC." should read – GEN1E LIFESCIENCES INC. –

Signed and Sealed this
Twenty-ninth Day of July, 2025

Coke Morgan Stewart
*Acting Director of the United States Patent and Trademark Office*